US008378151B2

(12) United States Patent
Perkins et al.

(10) Patent No.: US 8,378,151 B2
(45) Date of Patent: Feb. 19, 2013

(54) SYSTEMS AND METHODS FOR AN INTEGRATED SOLAR DRIVEN CHEMICAL PLANT

(75) Inventors: Christopher Perkins, Boulder, CO (US); Zoran Jovanovic, Louisville, CO (US); Courtland Hilton, Broomfield, CO (US); Wayne Simmons, Dublin, OH (US); Andrew Minden, Boulder, CO (US)

(73) Assignee: Sundrop Fuels, Inc., Longmont, CO (US)

( * ) Notice: Subject to any disclaimer, the term of this patent is extended or adjusted under 35 U.S.C. 154(b) by 288 days.

(21) Appl. No.: 12/796,121

(22) Filed: Jun. 8, 2010

(65) Prior Publication Data

US 2010/0249468 A1    Sep. 30, 2010

Related U.S. Application Data

(60) Provisional application No. 61/248,282, filed on Oct. 2, 2009, provisional application No. 61/185,492, filed on Jun. 9, 2009.

(51) Int. Cl.
C07C 29/00 (2006.01)
C07C 31/04 (2006.01)
C07C 1/04 (2006.01)
(52) U.S. Cl. .................... 568/840; 518/702; 204/157.15
(58) Field of Classification Search .................. 568/840; 204/157.15; 518/702
See application file for complete search history.

(56) References Cited

U.S. PATENT DOCUMENTS

| | | | |
|---|---|---|---|
| 1,508,464 A | 9/1924 | McFarland | |
| 4,164,123 A | 8/1979 | Smith | |
| 4,219,492 A | 8/1980 | Konoki et al. | |
| 4,247,755 A | 1/1981 | Smith, Jr. et al. | |
| 4,415,339 A | 11/1983 | Aiman et al. | |
| 4,455,153 A | 6/1984 | Jakahi | |
| 4,552,741 A | 11/1985 | Melchoir | |
| 4,704,137 A | 11/1987 | Richter | |
| 4,756,722 A | 7/1988 | Knop et al. | |
| 4,766,154 A | 8/1988 | Bonnell et al. | |
| 5,179,129 A | 1/1993 | Studer | |
| 5,581,998 A | 12/1996 | Craig | |
| 5,618,500 A | 4/1997 | Wang | |
| 5,647,877 A | 7/1997 | Epstein | |
| 5,906,799 A | 5/1999 | Burgie et al. | |
| 6,660,244 B2 | 12/2003 | Negishi et al. | |
| 6,676,716 B2 | 1/2004 | Fujimura et al. | |
| 6,872,378 B2 | 3/2005 | Weimer et al. | |
| 7,033,570 B2 | 4/2006 | Weimer et al. | |
| 7,207,327 B2 | 4/2007 | Litwin et al. | |
| 2002/0134019 A1 | 9/2002 | Paisley | |
| 2003/0208959 A1 | 11/2003 | Weimer et al. | |
| 2003/0213514 A1 | 11/2003 | Ortabasi | |
| 2004/0170210 A1 | 9/2004 | Do et al. | |
| 2004/0219079 A1 | 11/2004 | Hagen et al. | |
| 2005/0020700 A1 | 1/2005 | Bahnisch | |
| 2006/0024538 A1 | 2/2006 | Steinberg | |
| 2006/0096298 A1 | 5/2006 | Barnicki et al. | |
| 2006/0140848 A1 | 6/2006 | Weimer et al. | |
| 2006/0188433 A1 | 8/2006 | Weimer et al. | |
| 2006/0225424 A1 | 10/2006 | Elliott et al. | |
| 2007/0098602 A1 | 5/2007 | Haueter et al. | |
| 2007/0129450 A1 | 6/2007 | Barnicki et al. | |
| 2007/0225382 A1 | 9/2007 | Van Den Berg et al. | |
| 2008/0057366 A1 | 3/2008 | Katikaneni et al. | |
| 2008/0086946 A1 | 4/2008 | Weimer et al. | |
| 2008/0104003 A1 | 5/2008 | Macharia et al. | |
| 2008/0209891 A1 | 9/2008 | Johannes et al. | |
| 2008/0223214 A1 | 9/2008 | Palamara et al. | |
| 2008/0284401 A1 | 11/2008 | Oettinger et al. | |
| 2008/0293132 A1 | 11/2008 | Goldman et al. | |
| 2008/0302670 A1 | 12/2008 | Boyle | |
| 2008/0307703 A1 | 12/2008 | Dietenberger et al. | |
| 2009/0064578 A1 | 3/2009 | Theegala | |
| 2009/0093555 A1 | 4/2009 | Stites et al. | |
| 2009/0313886 A1 | 12/2009 | Hinman | |
| 2010/0000874 A1 | 1/2010 | Hinman | |

FOREIGN PATENT DOCUMENTS

| | | |
|---|---|---|
| JP | 2002/012877 A | 1/2002 |
| SU | 1763814 A1 | 9/1992 |

OTHER PUBLICATIONS

International Preliminary Report on Patentability for International Application No. PCT/US10/37911, dated Dec. 12, 2011, 9 pages.
International Preliminary Report on Patentability for International Application No. PCT/US10/37914, dated Dec. 12, 2011, 8 pages.
International Preliminary Report on Patentability for International Application No. PCT/US10/37923, dated Dec. 12, 2011, 13 pages.
International Preliminary Report on Patentability for International Application No. PCT/US10/37925, dated Dec. 12, 2011, 10 pages.
International Preliminary Report on Patentability for International Application No. PCT/US10/37930, dated Dec. 12, 2011, 13 pages.
International Preliminary Report on Patentability for International Application No. PCT/US10/37934, dated Dec. 12, 2011, 10 pages.

(Continued)

Primary Examiner — Sikarl Witherspoon
(74) Attorney, Agent, or Firm — Rutan & Tucker, LLP

(57) ABSTRACT

A method, apparatus, and system for an integrated solar-driven chemical plant that manages variations in solar energy are disclosed. In some embodiments, a chemical reactant, including particles of biomass, are converted in a solar driven chemical reactor into synthesis gas containing carbon monoxide and hydrogen using concentrated solar energy to drive the conversion of the chemical reactant. The synthesis gas is supplied for a catalytic conversion of the synthesis gas in a methanol synthesis plant to methanol. Cycling occurs between an operational state and an idle state for a number of methanol trains in the methanol synthesis plant depending upon an amount of synthesis gas generated in the solar driven chemical reactor. A control system for the chemical reactor sends control signals to and receives feedback from a control system for the methanol synthesis plant.

17 Claims, 11 Drawing Sheets

OTHER PUBLICATIONS

International Preliminary Report on Patentability for International Application No. PCT/US10/37938, dated Dec. 12, 2011, 10 pages.
International Preliminary Report on Patentability for International Application No. PCT/US10/37940, dated Dec. 12, 2011, 10 pages.
International Preliminary Report on Patentability for International Application No. PCT/US10/37944, dated Dec. 12, 2011, 10 pages.
Cross Reference to Related Applications Under 27 C.F.R. 1.78, 2 pages, Aug. 17, 2011.
International Search Report for PCT/US10/037911, dated Aug. 6, 2010, 2 pages.
International Search Report for PCT/US10/037914, dated Aug. 13, 2010, 2 pages.
International Search Report for PCT/US10/037923, dated Aug. 9, 2010, 3 pages.
International Search Report for PCT/US10/037925, dated Aug. 10, 2010, 3 pages.
International Search Report for PCT/US10/037930, dated Sep. 20, 2010, 5 pages.
International Search Report for PCT/US10/037934, dated Aug. 9, 2010, 2 pages.
International Search Report for PCT/US10/037938, dated Aug. 5, 2010, 2 pages.
International Search Report for PCT/US10/037940, dated Aug. 13, 2010, 2 pages.
International Search Report for PCT/US10/037944, dated Aug. 18, 2010, 2 pages.
Munzinger, M., et al., "Biomass Gass ification Using Solar Thermal Energy", *Anzses 2006*, pp. 1-10.
Mishra, Anuradha, et al., "Thermal Optimization of Solar Biomass Hybrid Cogeneration Plants", *Journal of Scientific & Industrial Research*, vol. 65, Apr. 2006, pp. 355-363.
Esser, Peter, et al., "The Photochemical Synthesis of Fine Chemicals With Sunlight," Angew. Chem. Int. Ed. Engl. 1994, vol. 33, pp. 2009-2023.

Multiple tube reactor

SYSTEMS AND METHODS FOR AN INTEGRATED SOLAR DRIVEN CHEMICAL PLANT

RELATED APPLICATIONS

This application claims the benefit of both U.S. Provisional Patent Application Ser. No. 61/248,282, filed Oct. 2, 2009 and entitled "Various Methods and Apparatuses for Sun Driven Processes," and U.S. Provisional Patent Application Ser. No. 61/185,492, titled "VARIOUS METHODS AND APPARATUSES FOR SOLAR-THERMAL GASIFICATION OF BIOMASS TO PRODUCE SYNTHESIS GAS" filed Jun. 9, 2009.

NOTICE OF COPYRIGHT

A portion of the disclosure of this patent document contains material that is subject to copyright protection. The copyright owner has no objection to the facsimile reproduction by anyone of the software engine and its modules, as it appears in the Patent and Trademark Office patent file or records, but otherwise reserves all copyright rights whatsoever.

FIELD OF THE INVENTION

Embodiments of the invention generally relate to systems, methods, and apparatus for chemical reactions. More particularly, an aspect of an embodiment of the invention relates to solar-driven systems, methods, and apparatus for refining biomass and other materials.

BACKGROUND OF THE INVENTION

The substance/substances initially involved in a chemical reaction are generally called reactants. Chemical reactions are usually characterized by a chemical change in the reactants, which then yields one or more products. Biomass gasification is an endothermic process. Energy must be put into the endothermic process to drive the chemical reaction forward. Typically, this is performed by partially oxidizing (burning) the biomass itself. Between 30% and 40% of the biomass must be consumed to drive the process, and at the temperatures which the process is generally limited to (for efficiency reasons), conversion is typically limited, giving still lower yields. In contrast, the proposed solar-driven biorefinery uses an external source of energy (solar) to provide the energy required for reaction, so none of the biomass need be consumed to achieve the conversion. This results in significantly higher yields of gallons of gasoline per biomass ton than previous technologies. As the energy source being used to drive the conversion is renewable and carbon free. Also, chemical reactors are generally engineered to operate at constant conditions around the clock, rather than on a cyclic basis.

SUMMARY OF THE INVENTION

A method, apparatus, and system for a solar-driven chemical plant that manages variations in solar energy are disclosed. Some embodiments include a method for harmonizing an integrated solar driven chemical plant.

A chemical reaction may be conducted in a solar driven chemical reactor having multiple reactor tubes using concentrated solar energy to drive the conversion of the chemical reactant. An endothermic chemical reaction is conducted in the reactor tubes with the heat of the concentrated solar energy. The chemical reaction includes one or more of the following: biomass gasification, steam methane reforming, methane cracking, steam ethane cracking to produce ethylene, or carbon dioxide splitting, using solar thermal energy coming from a concentrated solar energy field.

The products from the chemical reaction are supplied for a catalytic conversion of the products from the chemical reaction into a hydrocarbon fuel or other chemical in a chemical synthesis plant. The operation of the fuel synthesis plant is dependent upon an amount of synthesis gas generated in the solar driven chemical reactor.

The control system for the fuel synthesis plant sends control signals to and receives feedback from a control system for the chemical reactor. The control system for the chemical reactor at least indicates the amount of product being generated in the solar driven chemical reactor.

BRIEF DESCRIPTION OF THE DRAWINGS

The drawings refer to embodiments of the invention in which.

Figure 1:
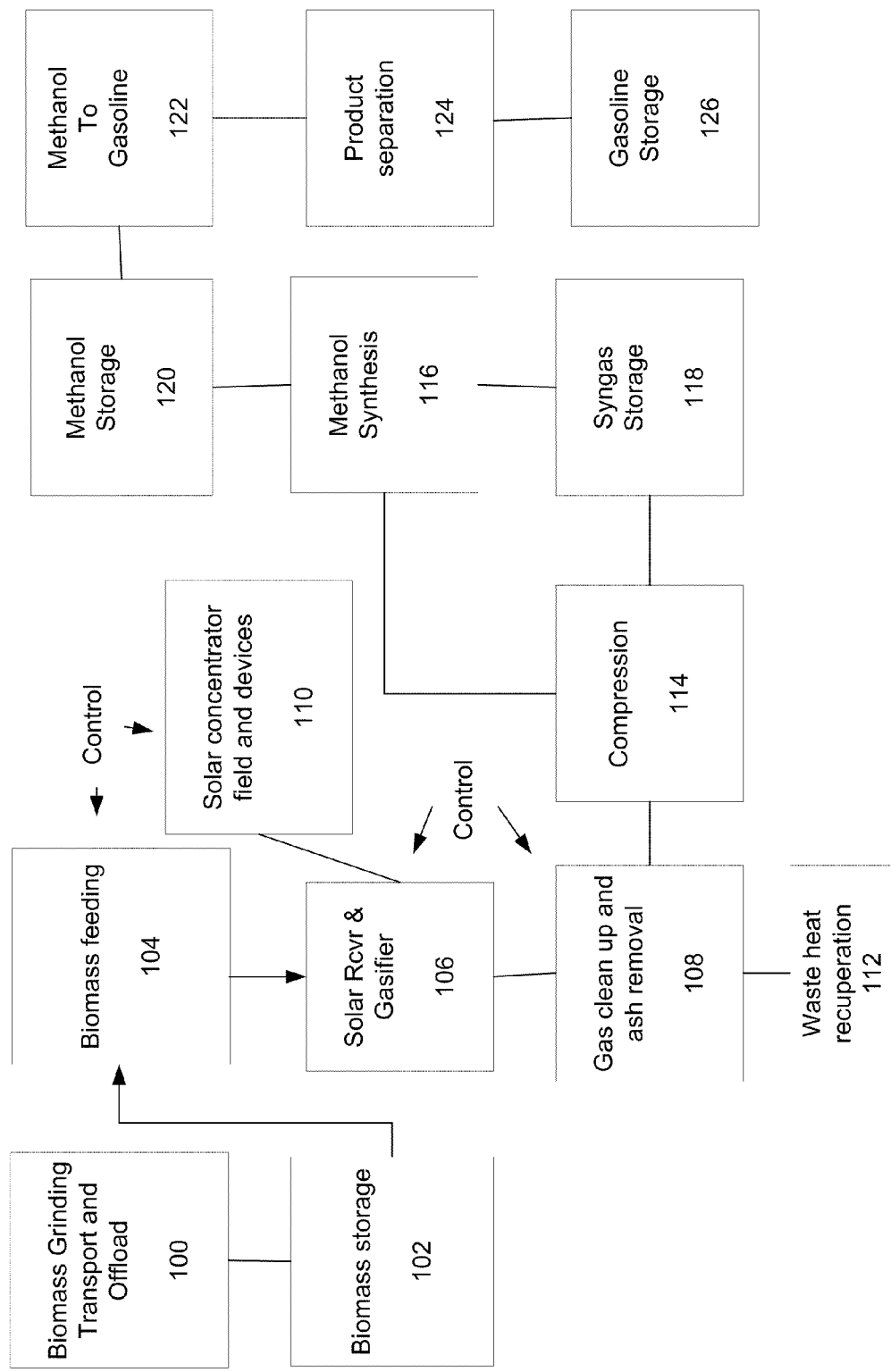
FIG. 1 illustrates a block diagram of an embodiment of an example process flow.

While the invention is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the invention.

DETAILED DISCUSSION

In the following description, numerous specific details are set forth, such as examples of specific data signals, named components, connections, number of reactor tubes, etc., in order to provide a thorough understanding of the present invention. It will be apparent, however, to one of ordinary skill in the art that the present invention may be practiced without these specific details. In other instances, well known components or methods have not been described in detail but rather in a block diagram in order to avoid unnecessarily obscuring the present invention. Further specific numeric references such as first reactor tube, may be made. However, the specific numeric reference should not be interpreted as a literal sequential order but rather interpreted that the first reactor tube is different than a second reactor tube. Thus, the specific details set forth are merely exemplary and features in one embodiment may be used in another embodiment. The specific details may be varied from and still be contemplated to be within the spirit and scope of the present invention. The term coupled is defined as meaning connected either directly to the component or indirectly to the component through another component.

In general, a method, apparatus, and system are described for an integrated solar-driven chemical plant that manages variations in solar energy.

A number of design mechanisms exist to make this integrated solar-driven chemical plant. A first design mechanism is creating storage, buffering, and idling processes established for the integrated plant to decouple the response rate of a first process step from the response rate of a second process step. The storage, buffering, and idling processes established for integrated plant also decouple the direct production rate of a first process step from the supply requirements of a second process step. A second design mechanism is having individual control systems for each process step along with a hierarchal control system to harmonize the operation of each process step relative to the operation of another process step based on anticipated or feedback changes of the other process steps. A third design mechanism is the start up sequence and order for the components making up the integrated plant. Thus, the overall system adjustments are made for the solar driven chemical plant to work as a whole rather than operate as independent specific component/process steps.

In an embodiment, a chemical reactant, including particles of biomass, are converted in a solar driven chemical reactor into synthesis gas containing carbon monoxide and hydrogen using concentrated solar energy to drive the conversion of the chemical reactant. The synthesis gas is supplied for a catalytic conversion of the synthesis gas in a methanol synthesis plant to methanol. Cycling occurs between an operational state and an idle state for a number of methanol trains in the methanol synthesis plant depending upon an amount of synthesis gas generated in the solar driven chemical reactor. A control system for the chemical reactor sends control signals to and receives feedback from a control system for the methanol synthesis plant. The example chemical synthesis plant integrated with an upstream solar driven reactor is a methanol synthesis plant and other chemical synthesis plants could be integrated as well.

FIG. 1 illustrates a block diagram of an example process flow. Some embodiments encompass a solar-driven-biomass gasification to liquid fuel/electrical process. The process might also include generation, chemical processing, or biochar, for solar generated syngas derivative product or other similar technical process. In a specific example implementation the process described is a solar-driven-biomass gasification to 'green' liquid fuel process. In an embodiment, this process includes one or more of the following process steps.

The integrated chemical plant includes several process steps including a grinding system 100 for making biomass particles and other chemical feed preparation process that is run on an as-needed basis, a chemical reactant feed system 104 that supplies chemical reactant, including the biomass particles, when the solar driven chemical reactor is at least its minimum operating temperature, a solar concentrating field process 110 that is stowed when not in use and aligned to focus the concentrated solar energy at the solar driven chemical reactor 106 at least near Sunrise. The solar driven chemical reactor process 106 is kept at or near operating temperature during off production hours, a compressor process 114 that switches stages of compressors between compressing and idling twenty four hours a day, a synthesis gas clean-up process 108, an intermediate chemical generation process 116 such as methanol synthesis, and a final stage chemical process 124 such as generation of a liquid hydrocarbon fuel process such as methanol to gasoline.

Some process steps may be started in parallel with other process steps, while others may run continuously and just change states from idle to operational.

Biomass grinding or densification, transport and offload 100 may be part of the overall process. Bales of the biomass can be compressed and densified by a compactor to facilitate transport to on-site via the densification achieved by the double compression.

A grinding system 100 couples through storage 102 to the entrained-flow biomass feed system 104. A conveyer brings the biomass to the grinding system that grinds biomass into particles via a mechanical cutting device cooperating with a set of filters with specific sized holes in the filters. The grinding system generates particles that have an average smallest dimension size between 200 microns (um) and 2000 um in diameter, such to fit through the holes in the filters, with a general range of between 500 um and 1000 um, and then the particles are loaded into a feed vessel such as a lock hopper system with a standard belt or pneumatic conveyer. The biomass may be in an embodiment non-food stock biomass. In other cases, food stock biomass or a combination of the two might also be processed.

Two or more feed line supply the particles of biomass having an average smallest dimension size between 50 microns (um) and 2000 um to the chemical reactor. An entrained gas biomass feed system uses an entrainment carrier gas to move a variety of biomass sources fed as particles into the solar driven chemical reactor.

A solar receiver and gasifier 106 may be used to break down the biomass. An example biomass gasifier design and operation can include a solar chemical reactor and solar receiver to generate components of syngas. The feedforward portion and the feedback portion of the control system adapts the operation of the reactor to both long and short term disturbances in available solar energy. Various solar concentrator field designs to drive the biomass gasifier can be used. Some example systems may include a solar concentrator, focused mirror array, etc. to drive biomass gasifier 110.

Quenching, gas clean up, and ash removal from biomass gasifier 108 occur to make the produced syngas useable for the next process step. Some gasses generated in the chemical reactor may be a waste product, while other gasses can be compressed 114 prior to storage 118 or sent directly for methanol synthesis 116. Methanol may then be stored 120 for later methanol to gasoline conversion 122.

A storage capacity of the synthesis gas and idling of the methanol trains is created to decouple a response rate of the methanol synthesis plant from the response rate of the solar driven chemical reactor. The storage capacity and idling processes established for the integrated solar driven chemical plant also decouples a direct production rate of the synthesis gas generated in the solar driven chemical reactor from the supply requirements of the methanol synthesis plant.

An on-site fuel synthesis reactor that is geographically located on the same site as the chemical reactor and integrated to receive the hydrogen and carbon monoxide products from the gasification reaction can be used in some embodiments. Additionally, the on-site fuel synthesis reactor has an input to receive the hydrogen and carbon monoxide products and use them in a hydrocarbon fuel synthesis process to create a liquid hydrocarbon fuel. The on-site fuel synthesis reactor may be connected to the rest of the plant facility by a pipeline that is generally less than 15 miles in distance. The on-site fuel synthesis reactor may supply various feedback parameters and other request to the control system. For example, the on-site fuel synthesis reactor can request the control system to alter the H2 to CO ratio of the syngas coming out of the quenching and gas clean up portion of the plant and the control system will do so.

In various embodiments, synthesis gas may be fed to another technical application.

Figure 2:
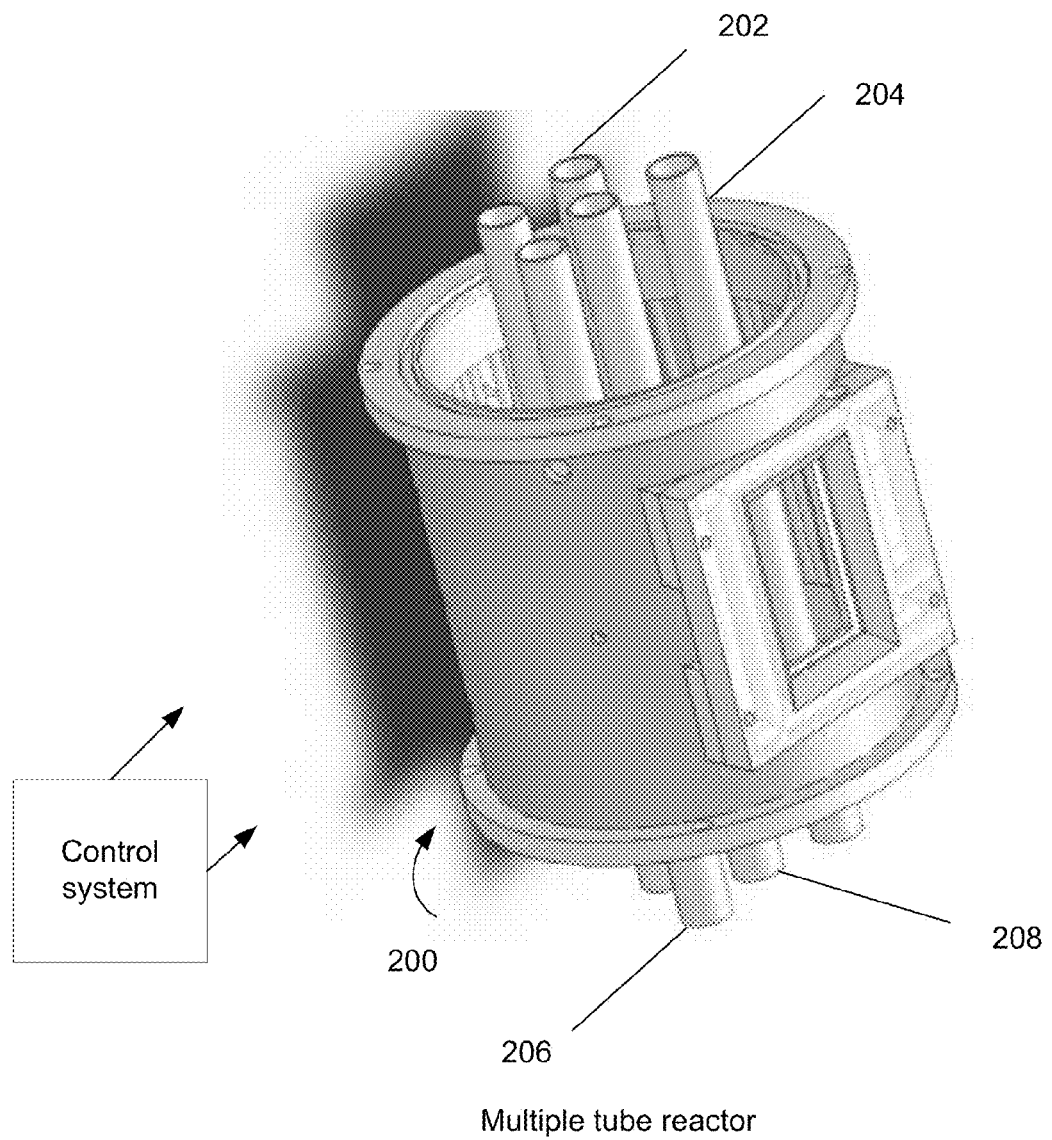
FIG. 2 illustrates a diagram of an embodiment of an example multiple tube reactor.

FIG. 2 illustrates a diagram of an example multiple tube chemical reactor that may be used in a solar driven system. The chemical reactor has multiple reactor tubes 202, 204, 206, 208. A separate entrainment line may be used for each of the gasifier reactor tubes 202, 204, 206, 208 in the chemical reactor 200.

Note, a chemical reactor is the container in which a chemical reaction occurs. Also, the chemical reactor may be a single reactor tube, or a set of reactor tubes. Thus, the chemical reactor may be a single reactor with multiple reactor tubes or multiple reactors each being a single reactor tube, or some other similar combination. Further, different chemical reactions may take place in different reactor tubes of the solar-driven chemical reactor. For example, Steam Methane Reforming may occur in a first set of reactor tubes and biomass gasification may occur in another set of reactor tubes making up the chemical reactor, which is at least partially contained in the solar thermal receiver. Also, different chemical reactions may take place within the same reactor tube at the same time. Also, the control system may control the chemical reactions occurring within the reactor tubes via a number of mechanisms as described herein. For example, the flow rate of the chemical reactants, such as biomass particles and carrier gas, into and through the reactor tubes is controlled, along with a concentration of each reactant flowing through the reactor tube. The control system may control each reactor tube individually, or in sets/groups of for example clusters of eighteen tubes, or all of the tubes in their entirety. The shape, orientation, and other features of the reactor tubes may vary. For example, they may be circular, square, elliptical, etc. and arranged in an arc pattern or circular pattern, etc. and as further described herein. Note, for contrast purposes, more than one chemical reactor may be located on a common tower such as in FIG. 3. The example shows a first chemical reactor, a second chemical reactor, and a third chemical reactor contained at least partially within its own associated solar thermal receiver. The first, second, and third chemical reactors located on the same tower may or may not share a common control system but do not share a common solar thermal receiver, and thus, are truly each distinct chemical reactors. However, they all may be fed from some common feed vessels/lock hoppers and/or may share downstream quenching and gas clean up system components.

Design Mechanism—Control System

The control system may operate in a networked environment using logical connections to one or more remote computers, such as a remote computer. The control system hardware may be one or more of a Programmable Logic Controller, via different data communication protocols using Personal Computer, Macintosh, CNC, neural nets, analog devices, with accompanying software applications and algorithms scripted to perform various functions, or various combinations of these systems.

The integrated plant has a hierarchal control system formed between the control system for each individual process step interacting with control signals and feedback signals with the other control systems. For example, the control system for the chemical reactor sends control signals to and receives feedback from 1) a control system for the compressors, 2) the control system for the methanol synthesis plant, 3) the control system for routing syngas to storage, the methanol synthesis plant, or to recirculate the syngas in the gas clean up, 4) the control system for the solar energy concentrator field as well as 5) other process steps. The hierarchal control system can harmonize an operation of one part of system to another process step in the system.

The control system for the solar driven chemical reactor and its multiple reactor tubes factors in many parameters in its control algorithms for chemical reactor operation. The control system controls balancing of mass in and energy needed to drive various chemical reactions verses available concentrated solar energy while still maintaining operational temperature of the chemical reactor within a set range and factoring in that each endothermic reaction consumes an amount of available energy AND the algorithm controls a concentration/amount of each reactant product into the chemical reactor to control the molarity and ratio of the reactants going into the reactions in order to control the products coming out of the reactions, AND the algorithm may control what chemical reactants are being supplied to the reactor; and thus, what chemical reactions are occurring within multiple reactor tubes. The control system 1) keeps a temperature at a high enough temperature for a substantially entire conversion of the chemical reactants, including particles of biomass, to product gases and elimination of tar products at least 1100-1300 degree C. to less than 200 mg/m^3 and 2) keeps a temperature low enough for the reactor tube wall temperature of less than 1600 degrees C. to not structurally weaken the walls or significantly reduce receiver efficiency and above a transitory low operational temperature of 800 degrees C.

The control system may have a feedforward and feedback portion configured to manage predicted changes in available solar energy as well as actual measured stochastic changes in available solar energy. The control system may balance the gasification reaction between biomass feed rate and an amount energy solar energy directed at the aperture of the receiver to keep a temperature at which the chemical reactor operates at 1) a high enough temperature for the greater than 90 percent conversion of the carbon content of the biomass to product gases including carbon monoxide and hydrogen as well as an elimination of tar products.

The control system may be configured to balance chemical reaction types, such as a biomass gasification reaction, a stream reforming reaction, a dry reforming reaction and various combinations of these reactions within the solar driven chemical reactor, to an amount of concentrated solar energy available directed at a solar thermal receiver containing the chemical reactor in order to keep the solar chemical reactor at a temperature at which the chemical reactor operates high enough to maintain the generated syngas within the desired molar ratio of H2 to CO ratio of 2.1 to 2.8:1 with being substantially tar free having less than 200 mg/m^3 of tar, and having less than 7% by volume CO2 in the generated syngas. The control system uses a combination of controlling an amount of steam, natural gas, biomass particles, other chemical reactants and inert particles flowing in the tubes to keep the generated syngas within the desired thresholds.

The control system may be configured to balance the gasification reaction of biomass particles with the available concentrated solar energy and additional variable parameters including a fixed range of particle sizes, operating temperature of the chemical reactor, and residence time of the particles in a reaction zone in the chemical reactor so that an overall biomass particle conversion remains above a threshold set point of greater than 90 percent of the carbon content of the particles into reaction products that include hydrogen and carbon monoxide gas with low tar production of less than 200 mg/Nm^3 and preferably less than 50 mg/Nm^3, where the residence time of the particles of biomass in the reaction zone in the chemical reactor is between a range of 0.01 and 5 seconds.

A feed demand signal from the control system may control the feed rate of particles of biomass in the solar driven chemical reactor by a feedforward/feedback model-predictive control system in cooperation with designing in enough surface area, thermal mass, and heat capacity in the multiple tubes and receiver cavity to ensure that temperature of the reactor cavity remains in the operational temperature range of below 1600 degrees C. and above 800 degrees C. during the rapidly changing daily weather conditions. The feed forward model predicts an available solar energy over each time period in a given day as well as each day throughout the year. The feedback portion receives dynamic feedback from sensors, including temperature sensors, and the sensor feedback and weather predictions are combined to maintain both the quality and output of resultant syngas at above the threshold set point of substantial tar destruction resulting in less than or equal to 50 mg/m^3 and gasification of greater than 90 percent of the carbon content of the biomass particles into the reaction products. Enough surface area and thermal mass are designed/built into the cavity of the solar receiver and multiple reactor tubes, to act as a ballast, averaging out very short term small fluctuations (second to second) in the available solar energy to have a very low ramp-up and ramp-down of temperature of the receiver and reactor due to these instantaneous changes in available solar energy, thereby allowing the ramp-up and ramp-down of the feed rate of biomass particles to be more gradual as well.

The solar-driven chemical reactor has a cyclic operation due to weather events and daily diurational effects rather than a continuous steady state operation. The computerized control system controls the feed rate of the chemical reactants including particles of biomass material, into the two or more reactor tubes with well-controlled feed rates and changes the feed rate of the biomass material based on changing solar availability given as feedback to the computerized control system by the sensors and the predictive models. The feedforward portion and the feedback portion of the control system may be adapted for both long and short term disturbances in available solar energy. The feedforward portion anticipates cyclic changes in solar energy due to at least a time of day, day of the year, short-term cloud, dust, smoke or other obscuring events, or long-term weather events, with a predictive model that adapts to the anticipated cyclic changes. The feedback portion measures actual process parameters including the operating temperature of the chemical reactor and then uses these measurements in the balancing of the gasification reaction of biomass particles.

Thus, the control system may utilize different models and/or controls schemes that may be automatically or manually selected depending on the system and variable state. For example, insolation event perturbation may be categorized into 3 types: 1) short events, e.g. 0-5 hours, often caused by passing clouds, 2) medium events, e.g. 5-14 hours, often caused by diurnal effects, and 3) long-term events (e.g. 14 hours or more) generally caused by major weather systems.

Balancing the amount of biomass particles flowing into each of the reactor tubes to an amount of solar energy available is accomplished via the control system to control flow in the individual reactor tubes by controlling a rotational rate of a screw of a lock hopper feeding the biomass where all of the tubes in the tube subset being supplied by this lock hopper have their feed rate simultaneously turned up or turned down. Alternatively, the computerized control system may be configured to send a signal to vary an amount of the reactor tube-subsets participating in the gasification reaction by turning on or turning off a flow of particles of biomass from the feed vessel to the reactor tubes making up a tube subset.

Figure 3:
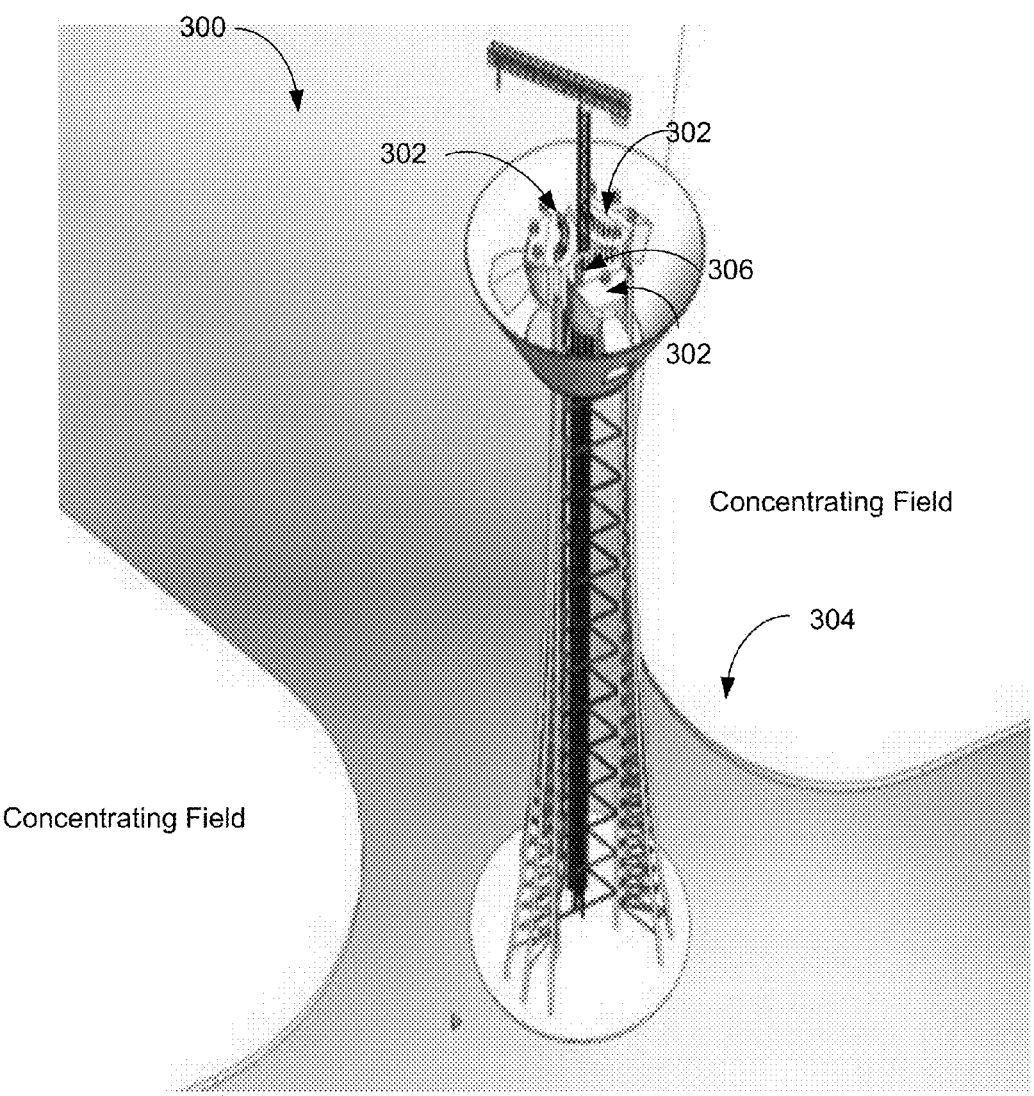
FIG. 3 illustrates a diagram of an embodiment of an example solar tower with receivers and solar energy concentrating fields.

FIG. 3 illustrates a diagram of an example solar tower 300 with receivers 302 and solar energy concentrating field 304. A solar tower 300 may be used in the solar-driven chemical plant with the entrained-flow biomass feed system. The feed system can be feedstock flexible via, for example, particle size control of the biomass.

Multiple solar thermal receivers may be used in the integrated system. Each solar thermal receiver 302 contains a chemical reactor 306 and the multiple solar thermal receivers share a common tower. A chemical reactor 306 in each receiver 302 receives concentrated solar thermal energy from one or more solar energy concentrating fields 304 including 1) a single mirror, heliostat, or solar-concentrating dish, 2) an array of heliostats, 3) two or more solar-concentrating dishes, and 3) any combination of the three.

The heliostats may be aligned with the one or more apertures in the cavity. The apertures can be, for example, sized to have a high average concentration of solar energy greater than 500 and preferably greater than 1000 suns at the one or more apertures.

Figure 5:
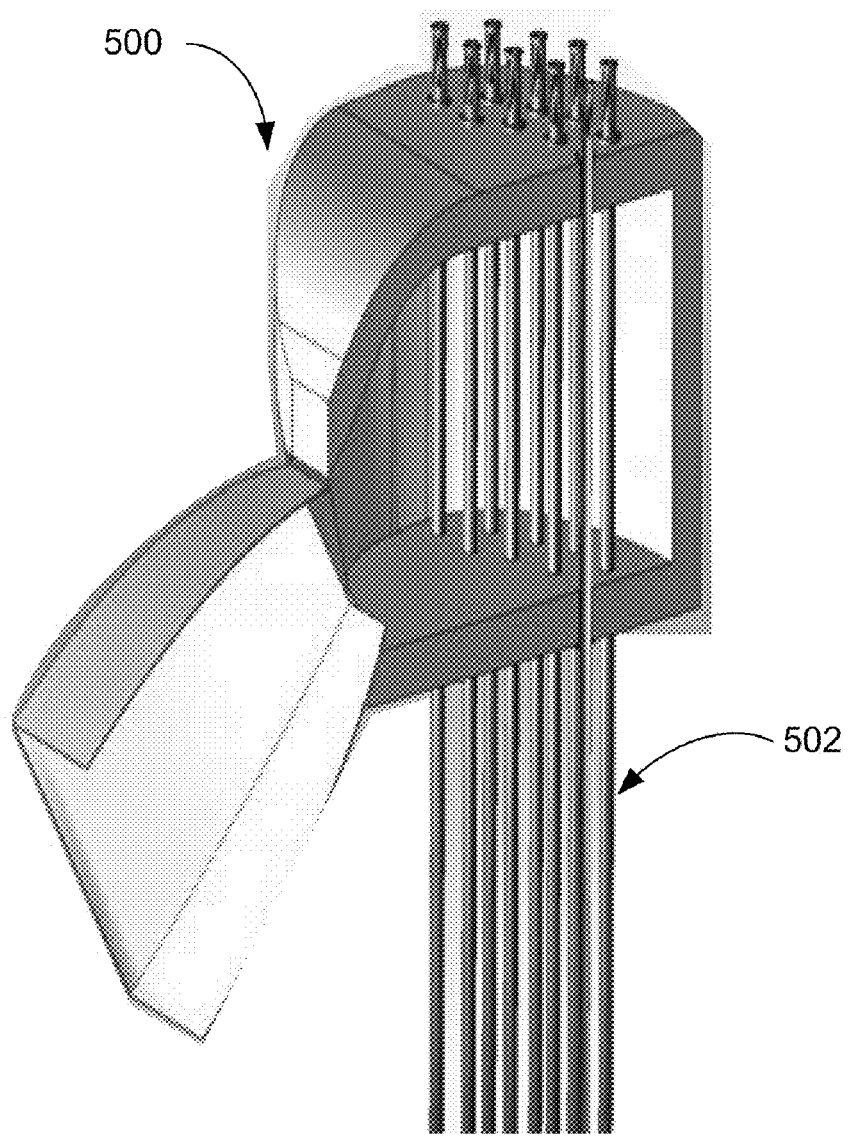
FIG. 5 illustrates a diagram of an embodiment of a solar thermal receiver with gasifier tubes.
Figure 6A:
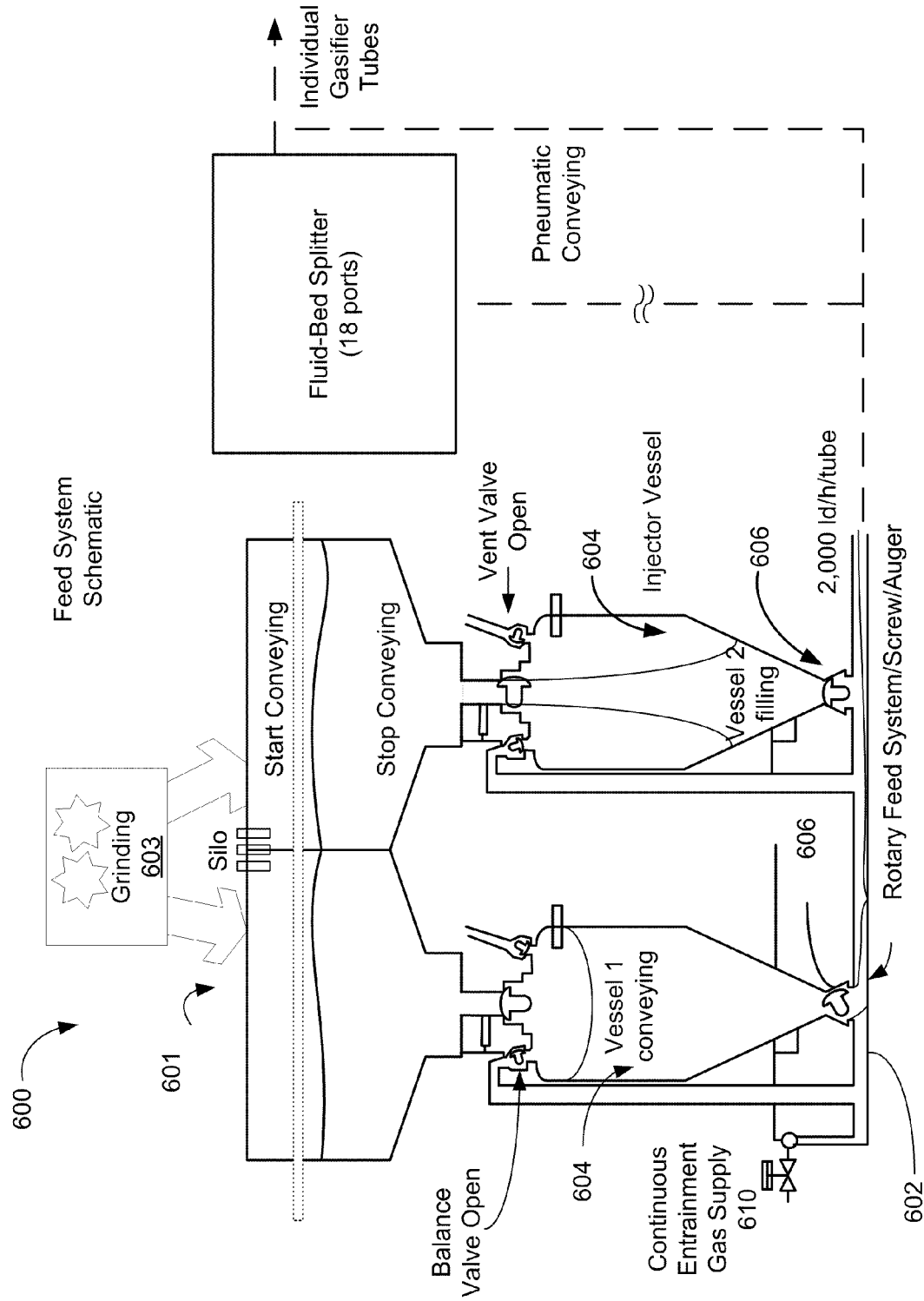
FIGS. 6a and 6b illustrate block diagrams of embodiments of the entrained-flow biomass feed system.
Figure 6B:
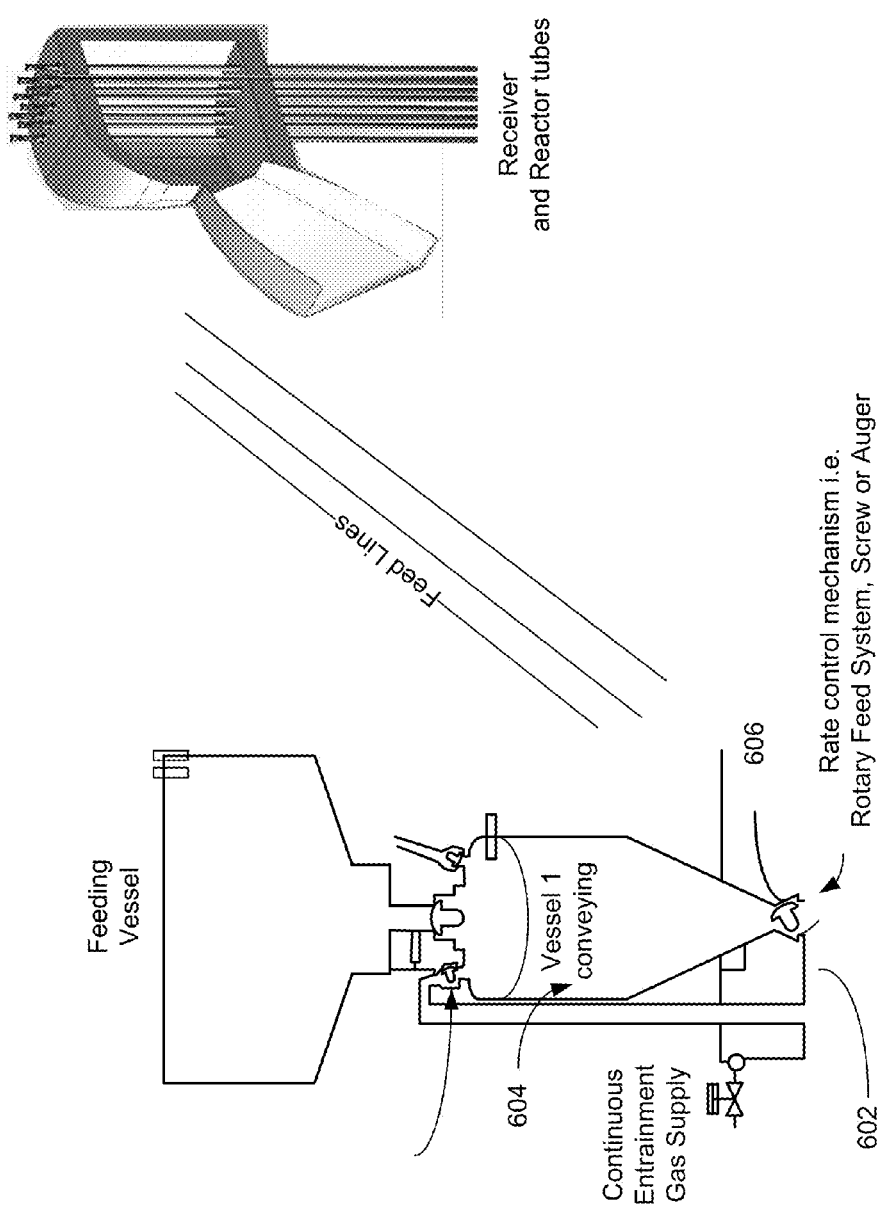
Figure 7:
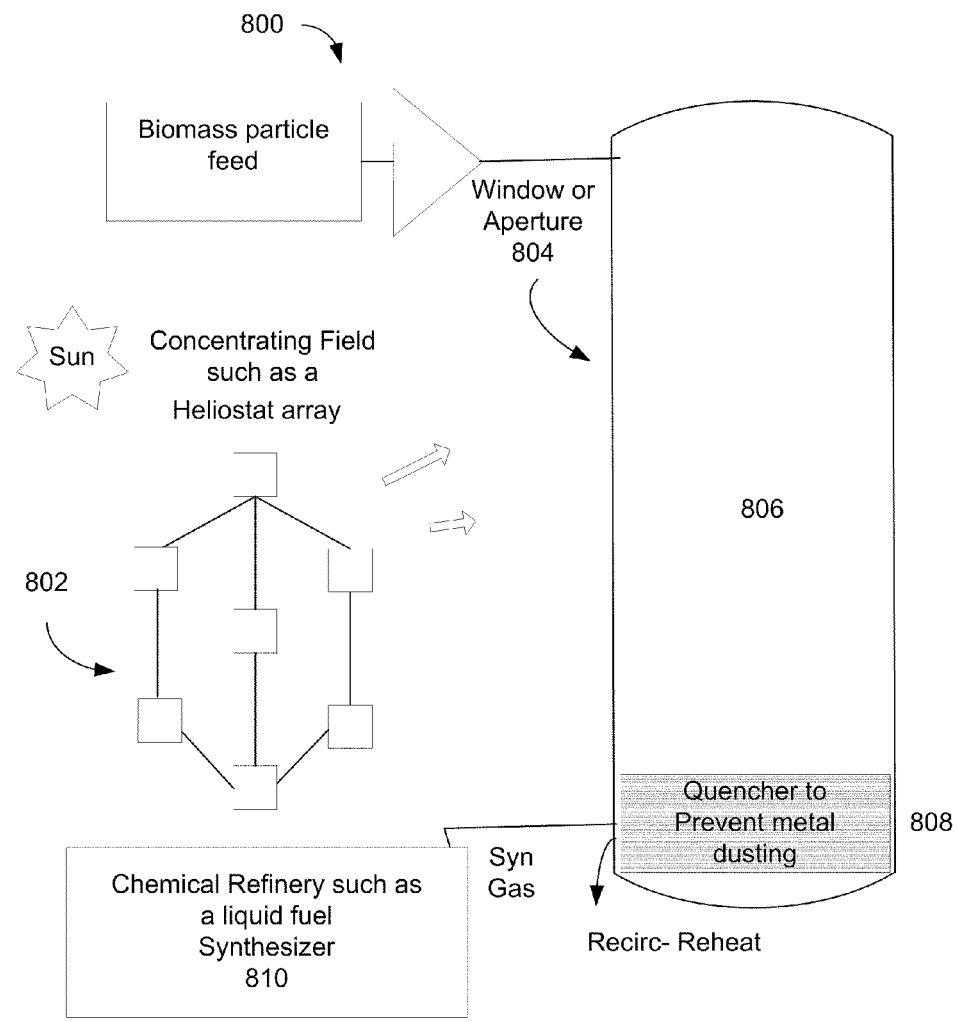
FIG. 7 illustrates a diagram of an embodiment of a solar-driven chemical plant.

FIG. 5 illustrates a diagram of a solar thermal receiver 500 with gasifier tubes 502. The solar-driven chemical plant includes the solar driven chemical reactor 502 and the solar thermal receiver 500. In some embodiments, solar thermal receiver 500 can enclose the multiple reaction tube downdraft chemical reactor. Thus, the solar-driven chemical reactor may have multiple reaction tubes in a downdraft orientation. As discussed, the feed system feeds the biomass particles into the multiple reaction tubes, in which the particles of biomass are gasified in the presence of steam at a temperature exceeding 950 degrees C. from an exit of a gasification reaction zone of the reactor tubes to generate the at least hydrogen and carbon monoxide products from the gasification reaction. The control system controls the feed system and concentrating solar energy fields to maintain the temperature of the reactor tubes of the chemical reactor at a steady state temperature generally exceeding 1000 degrees C., above the transitory minimum temperature of 800 degrees C. and below peak temperatures of 1600 degrees C.

The computerized control system is configured to receive a feedback signal from a set of sensors. An amount of solar energy available can be indicated by one or more temperature sensors in the chemical reactor and one or more light meters provides the actual process parameters information to the feedback portion of the control system.

One or more temperature sensors detect the current operating temperature of the chemical reactor, such as at the entrance and the exit, and supply that measurement to the feedback portion of the control system.

The feed vessel may respond to a feed demand signal from the computerized control system. The computerized control system controls a flow rate of particles of biomass in the solar-driven chemical reactor based on an amount of solar energy available indicated by sensors for the chemical reactor including temperature sensors and/or light meters.

Another sensor, a composition analyzer senses changes in chemical composition at the exit of the chemical reactor for two or more possible effluent chemicals including hydrogen, carbon monoxide, methane, tar composition, carbon dioxide, sulfide or any combination thereof of the syngas. The composition analyzer provides a dynamic signal to the feedback portion of the control system to keep these compositions within the desired ranges. Upon readings of chemical compositions, such as methane, hydrogen, carbon monoxide, and/or tar composition of the syngas that are above a threshold, the control system may send a signal to divert the reactant products of the gasification reaction to a recycling line back into the entrance to the chemical reactor to avoid damage to filters, compressors, catalytic systems, and other components in the downstream portions of the integrated solar driven chemical plant process.

The control system can turn on and off the resistance heaters as additional heat sources for maintaining temperature as need be. The control system sends control signals the solar energy concentrating fields to align the solar energy concentrating field and control temperature of the solar driven chemical reactor. The control system supplies a control signal to and receives feedback from 1) a chemical reactant feed system, 2) a solar energy concentrating field, 3) a supplemental heating system for idle periods, 4) the methanol synthesis plant, and 5) other plant processes. The lag times and response times of the 1) solar energy concentrating fields to alter alignment and an amount of concentrated solar energy supplied, 2) feed system to alter an amount of biomass flowing in the reactor tubes, 3) time for weather events to alter an amount of solar energy available, and 4) time to alter syngas composition including H2:CO ratio for methanol synthesis, and 5) an amount of solar generated syngas that is currently being and predicted to be generated are all factors taken into account by a control algorithm in the control system in sending out the control signals to the feed system, the solar energy concentrating fields, the methanol synthesis plant, and the supplemental heating system.

A shape of the cavity of the receiver is designed so that parameters of an average temperature in the cavity and the average concentration of solar energy at the one or more apertures act to control calculable radiative losses from the cavity. Thus, the receiver cavity temperature is a controlled parameter, which the control system then primarily controls by modulating a flow rate of biomass particles through the reactor tubes balanced against the predicted feedforward available amount of solar energy and the dynamically determined feedback amount of available solar energy.

Figure 4:
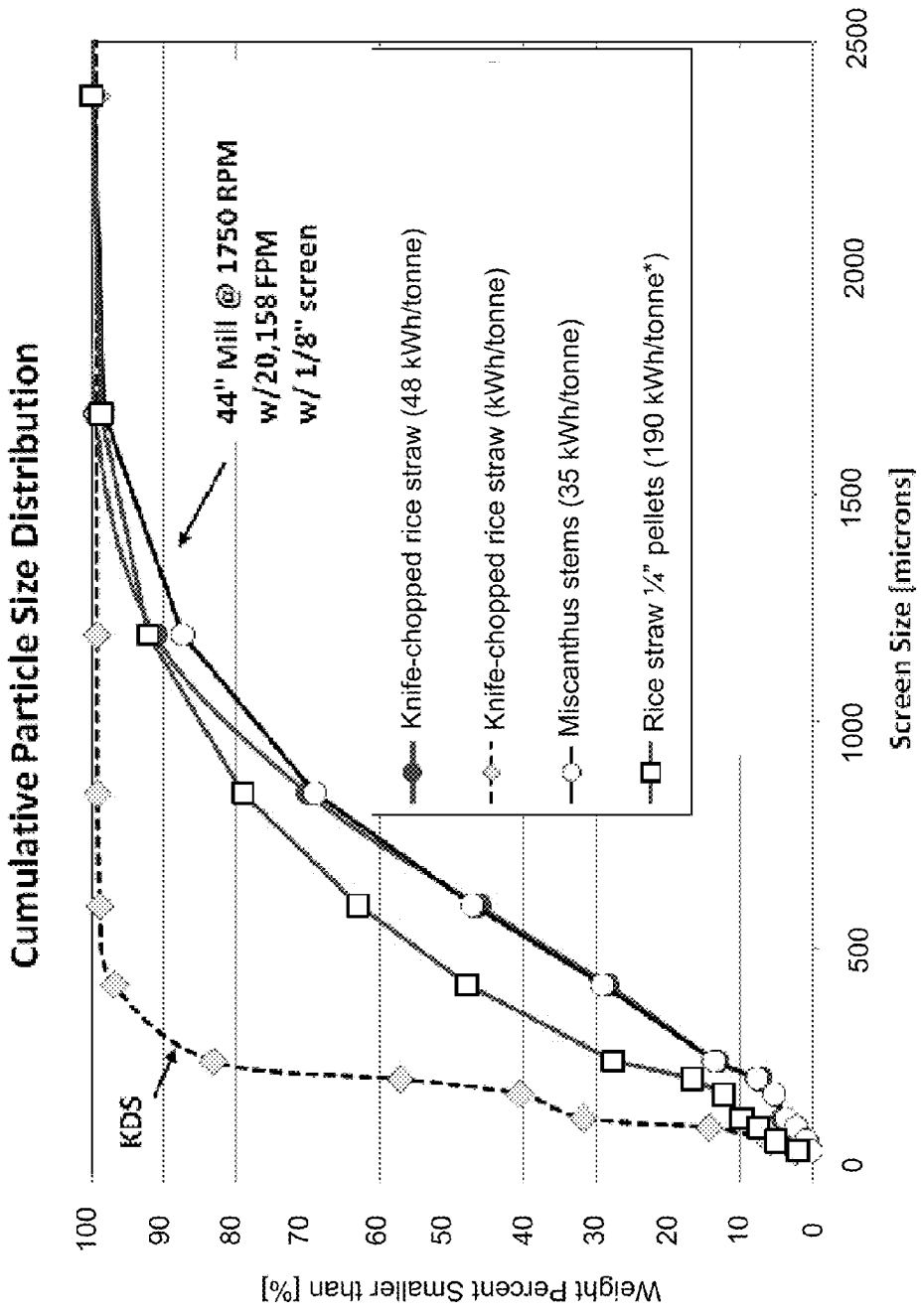
FIG. 4 illustrates a graph of an embodiment of particle size distribution of representative biomass material.

In an embodiment, two or more reactor tubes in the chemical reactor in which the biomass particles flow in are located within the solar thermal receiver. One or more feed lines supply to the reactor tubes the particles of biomass in the fixed range of particle size controlled to an average smallest dimension size between 50 microns (um) and 2000 um, with a general range of between 200 micrometer and 1000 micrometer. See FIG. 4 for more biomass types and sizes.

As discussed, the solar-driven chemical reactor has multiple reactor tubes located inside the cavity of solar thermal receiver. Where in the multiple reactor tubes a chemical reaction driven by radiant heat occurs. For example, in the multiple reactor tubes particles of biomass are gasified in the presence of a steam (H2O) carrier gas and methane (CH4) in a simultaneous steam reformation and steam biomass gasification reaction to produce reaction products that include hydrogen and carbon monoxide gas using the solar thermal energy from the absorbed concentrated solar energy. The reactor tubes gasify the particles of biomass in the multiple reactor tubes of the chemical reactor in the presence of one or more of the following chemical reactants in the tubes: (i) biomass particles and steam (ii) biomass particles, methane, and steam, (iii) methane and steam (SMR). The different reactor tubes within the same receiver are constructed of a material to operate with the different chemical reactants. The inside walls of the reactor tubes are made of corrosion resistant materials with a resistance to steam of between a good to excellent rating.

Also, there may be excess water in the reactor for the straight biomass gasification reaction by itself. Hence, reactor tube materials are oxidation resistant and steam resistant. Down stream of the reactor, one or more knock out drums may exist to remove the excess water from the generated syngas and the inside walls of the reactor tubes that are made of corrosion resistant materials to with a resistance to steam of between a good to excellent rating.

Note, a chemical reaction in the solar driven chemical reactor using concentrated solar energy drives the conversion of the chemical reactant. An endothermic chemical reaction conducted in the reactor tubes may include one or more of the following: biomass gasification, steam methane reforming, methane cracking, steam ethane cracking to produce ethylene, or carbon dioxide splitting, using solar thermal energy coming from a concentrated solar energy field.

One or more apertures in the receiver are 1) open to an atmosphere of the Earth or 2) covered with a transparent window, to pass the concentrated solar energy into the solar thermal receiver to impinge on the multiple reactor tubes and cavity walls of the receiver and transfer energy by absorption and re-radiation, convection, and conduction to the reactants in the chemical reaction to drive the endothermic chemical reaction flowing in the reactor tubes.

An insulation layer around the cavity may be set thick enough to control conduction losses to less than 2% of the peak solar input. The insulation on an outside shell of the receiver maintains heat during operations and overnight during shutdown. The insulation may be set thick enough to keep conductive losses to less than 10% during operations and includes one or more from the group consisting of ceramic brick, ceramic blanket, combinations of the two.

The thick layer of insulation around a solar thermal receiver containing the chemical reactor is set to limit heat losses by conduction from a cavity of the receiver in conjunction with a moveable insulative door that covers a receiver aperture to limit heat losses by radiation, conduction, and convection from leaving the cavity during periods of non-operation, including inclement weather or nighttime, so that the temperature in the cavity is decreased by less than 400° C. in a 12 hour period when no concentrated solar energy is directed at the cavity aperture. The insulation and door maintain heat energy to reduce both 1) the amount of time required to heat the receiver and reactor tubes following a down period and 2) the thermal shock and stresses imparted to the receiver and reactor materials of construction.

Thus, the high temperature door is used to mechanically cover and seal the receiver during long periods of being shut down to minimize heat loss and preserve the environment in the receiver cavity.

A small boiler or resistance heaters connected to the outside shell of the receiver to may be used to aid in temperature control of the chemical reactor. Molten salts may capture waste heat from the quenching of the effluent gas stream from the chemical reactor and use this energy to drive the electrical generation the heaters or steam generation of the boilers.

A chamber of the solar thermal receiver contains additional radiant heat masses to the reactor tubes, which have high temperature (>1400° C.) capable storage material that absorb the concentrated solar energy. The radiant heat masses are used to keep the reactor tubes hot during long periods of off sun, during cyclic up and down times in the plant, as well as keep temperature in the reactor less transient during normal operation when instantaneous solar flux can vary. The one or more additional fixed radiant heat structures are located within the cavity to store additional heat energy. The amount of stored heat in the mass of the walls of the receiver, tube walls and additional fixed radiant heat structures is set for a transfer of heat radiation from walls of the receiver, tube walls, as well as the one or more additional fixed radiant heat structures to transfer at least enough heat to the particles of the biomass in the aerosol stream to gasify and convert the biomass reactant into the greater than 90 percent gasification of the biomass particles into the reactant products during intermittent periods of the day when the Sun is partially or completely blocked by clouds.

FIGS. 6*a* and 6*b* illustrate block diagrams of embodiments of the entrained-flow biomass feed system 600.

One or more feeding vessels in the biomass feed system supply two or more reactor tubes in the solar-driven chemical reactor. One example solar-driven chemical plant may include the entrained-flow biomass feed system 600 that includes or otherwise cooperates with a grinding system.

The grinding system 603 has a mechanical cutting device used to grind the biomass into primary particles, which are to be fed into the solar driven chemical reactor. The grinding system supplies primary particles that have an average smallest dimension size between 200 microns (um) and 2000 um, with a general range of between 500 um and 1000 um to a lock hopper system 604 with a standard belt conveyer. The biomass particles are then fed across a pressure boundary into a pressurized entrainment gas for feeding into in the solar driven chemical reactor. The feeding vessel may use an Auger/Screw feeder or an airlock-type rotational solids feeding/rate metering device.

The lock hopper has one or more outputs, which then feed the primary biomass particles across a pressure boundary into the pressurized entrainment carrier gas for feeding via the one or more feed lines into the solar-driven chemical reactor (see FIGS. 6*a* and 6*b* as well). A common entrainment gas line may feed a flow splitter and then split off to individual reactor tubes or separate entrainment gas lines may each feed a corresponding individual reactor tube. The entrainment gas biomass feed system uses an entrainment carrier gas (such as natural gas, steam, air, and/or any combination) and supplies a variety of feed stock biomass sources fed as particles into the solar driven chemical reactor. Generally the entrainment carrier gas will be natural gas, steam, and/or any combination. The entrained-flow biomass feed system has a gas source for the entrainment carrier gas.

The feeding vessel may be a lock hopper rotary feed system having an output to distribute the particles of biomass to the reactor tubes, which allows for balanced feeding to individual reactor tubes. The feed vessel may vary a feed rate of chemical reactant through the reactor tubes in a number of implementations. The control system sends signals to the different process steps of the integrated solar driven chemical plant including the chemical reactant feed system process and likewise receives feedback signals from many of the process steps.

Control of the multiple reactor tubes is split into two or more groups of tube subsets. Each single outlet or multi-outlet lock hopper provides and controls an amount of distribution of the biomass particles to the one or more pressurized entrainment lines that feed the two or more reactor tubes within a tube subset in the solar-driven chemical reactor. Two or more tube subsets make up the reactor tubes in the solar driven chemical reactor.

A separate biomass entrainment/feed rate metering line may be used for each of the reactor tubes in the chemical reactor, which allows independent temperature control and balancing of an amount of particles of biomass or other chemical reactants flowing in each of the reactor tubes in the multiple tube solar-driven chemical reactor. The separate entrainment line and metering device of the entrained-flow biomass feed system for each individual or tube set of reactor tubes in the chemical reactor also allows balancing of 1) an amount of particles of biomass or other chemical reactants flowing through the feed line to each reactor tube to 2) an amount of solar energy available for that reactor tube in the multiple tube solar driven chemical reactor.

The feeding vessel may be a lock hopper having an airlock type of feeding rate metering device and varies an amount of biomass being supplied to the two or more reactor tubes based on an amount of available concentrated solar energy to a heat sink affect to the chemical reactor and solar thermal receiver from the supplied amount of biomass in order to generate the at least hydrogen and carbon monoxide products from the gasification reaction at a greater than 90% conversion rate of the biomass in a residence time of 0.01 seconds to 5 seconds.

Two or more multiple outlet lock hoppers may be used in the entrained-flow biomass feed system. Each multi-outlet lock hopper feeds the biomass particles at the consistent volumetric amount of biomass particles into a reactor tube subset via one or more pressurized entrainment lines that feed the solar-driven chemical reactor.

A screw may be located in the lock hopper rotary feed system. The feed rate of the particles of biomass may be controlled by a weight measuring metering device and by controlling a rotational rate of the screw that moves set amounts of biomass along the axis of rotation. A computerized control system sends a feed demand signal to the screw and weight measuring metering device to control the feed rate of the particles of biomass in the individual gasifier reactor tubes in the solar-driven chemical reactor based on an amount of solar energy available indicated by sensors including temperature sensors and/or light meters.

The feeding vessel in the feed system may be configured to discharge the particles of biomass through a multiplicity of single-outlet rotational feed devices that provide the consistent volumetric feed rate. Each rotational feed device feeds a separate gas entrainment line. The rotational speed of each of the rotational feed devices is controlled independently, and each of the rotational feed devices feeds a separate reactor tube.

A flow enhancer, including bulkmatology flow enhancer or a porous-walled tube, in the entrained-flow biomass feed system to control an amount of entrainment carrier gas carrying the particles of biomass entering a gasification reaction zone of the reactor tubes by reducing velocity of the carrier gas just prior to an entrance to a gasification reaction zone of the reactor tubes by removing a controlled portion of the carrier gas through the flow enhancer. A computerized control system in the entrained-flow biomass feed system may be configured to balance the amount of biomass particles flowing in each of the reactor tubes based on an amount of solar energy available by controlling the resistance to flow in each tube via the addition or removal of carrier gas through the flow enhancer.

FIG. 7 illustrates a diagram of a solar-driven chemical plant 800. In such a system solar power from a concentrating field 802 may be provided through a window or aperture 804 to a solar heated reactor chamber 806. A quencher 808 may be used to prevent back reaction. As illustrated, biomass particles flow into the system at 810 and syngas flows out. Additionally, a heat exchange may occur between the biomass particles and the syngas.

In reactor 806 biomass particles can be reduced to syngas, which in turn can be synthesized into liquid fuel in liquid fuel synthesizer 808.

A quench zone is located near the exit of the gasification reaction zone of the reactor tubes. One or more injection pipes in the quench zone directly inject a cooling compound consisting of at least one of 1) low temperature water (H2O), 2) methane (CH4) with low temperature water, 3) low temperature methanol (CH3OH), and 4) various combinations into the syngas tubes and/or manifold carrying the effluent stream of the reactor tubes to simultaneously 1) rapidly cool the syngas stream of reaction products from the at least 1000 degree C. to less than 400 degrees C. and 2) provide chemical compounds necessary to achieve a proper H2 to CO ratio of syngas necessary for fuel synthesis. The energy to cause the endothermic reactions comes from heat contained in the reaction product syngas stream. The proper H2 to CO ratio of syngas composition necessary for fuel synthesis may be a 2:1 to 2.8:1 H2 to CO ratio. The chemical compounds of the cooling compound necessary to achieve the proper H2 to CO ratio of syngas composition necessary for fuel synthesis include one or more of the group consisting of:

1) water injected to mix with the reaction product syngas stream in order for an exothermic water gas-shift reaction to occur (CO+H2O→CO2+H2+energy) for increasing hydrogen and decreasing carbon monoxide, 2) carbon dioxide supplied with natural gas used as an entrainment gas, and/or generated in the biomass gasification reaction and becomes part of the reaction product syngas stream in order for decreasing hydrogen and increasing carbon monoxide in an endothermic reverse water-gas shift reaction to occur (CO2+H2+energy→CO+H2O), and 3) methane, and low temperature water supplied and mixed with the reaction product syngas stream in the presence of a catalyst to drive the endothermic steam reformation of methane to occur (CH4+H2O+energy→3H2+CO) for increasing an amount of hydrogen relative to the carbon monoxide.

The syngas generated with the proper CO:H2 ratios is cleaned up with filters to remove undesired chemicals, ash and other particles. The cleaned up synthesis gas is fed to a methanol synthesis plant and excess amounts of generated syngas are sent to syngas storage.

Multiple methanol reactor trains are operated in parallel from a common input of 1) syngas from either 1) a solar driven chemical reactor and 2) syngas from a storage tank or a combination of both. The fuel synthesis portion of the control system controls the operation of the multiple trains by potentially idling one or more of the methanol reactor trains based on feedback from the amount of synthesis gas being generated by the solar driven chemical reactor, which is subject to marked variations in volume of syngas output based on a seasonal, diurnal and weather effects. Thus, the multiple methanol reactor trains are individually controllable to be cycled between the idle state and the operational state due to the variable amount of syngas being fed into the process from the solar driven chemical reactor.

The multiple methanol reactor trains may be physically separate reactor trains in parallel. The multiple methanol reactor trains may also be physically a common reactor with a manifold that feeds multiple virtual reactor trains from that manifold but all incased in the shell of the common reactor. The methanol trains have an input coupled to receive synthesis gas from the upstream solar driven chemical reactor.

The downstream fuel synthesis process must have its parameters controlled to account for the cyclic supply of solar generated syngas as a feed product. Two points.

1) Thus, the methanol synthesis control system may control parameters including chemistry, temperature, and pressure of the methanol synthesis plant during idle non-production periods of time so that the methanol synthesis plant may rapidly resume to generating product methanol when the supply of solar generated syngas resumes in sufficient quantities.

2) Also, the methanol synthesis control system may control parameters including chemistry, temperature, and pressure of the methanol synthesis plant during idle non-production periods of time so that the methanol synthesis plant has little to no loss in catalytic activity or throughput over the plant's lifetime. This allows for the protection of the catalyst, as long as the syngas and product methanol gas are kept at a certain temperature and pressure, then the gases remains vaporized and does not condense on the catalyst prolonging the life of the catalyst.

The temporarily idled methanol reactor train(s) is kept at or near the reaction temperature with heat makeup as required to offset heat losses. Being at or near reaction temperature or pressure for an idled reactor when at least one other reactor is operating generally means being with 70 percent of the operating temperature and pressure. The layers of insulation around the methanol reactor train keep the plant near reaction temperature. Also, an example embodiment of this is the use of boiling water (shell and tube) reactors that are heated from an external boiler. The methanol synthesis reaction is exothermic and thus produces heat. The shells of each reactor train may be interconnected such that the hot compressed fluid removing the exothermic heat from a train that is operating is circulated around idle trains to keep the idle trains near reaction temperature. Also, waste heat from other areas of the plant such as the quenching operation on the syngas coming out of the solar driven chemical reactor may be stored in a hot salt or even as steam for later use. Note, during the operation of the solar driven reactor when the weather events are not blocking the Sun, massive amounts of excess heat exist in the syngas gas products coming out of that chemical reactor and need to be rapidly cooled/quenched. This waste heat captured during the quench may be stored as steam or hot salts and used later as a heat source when the weather conditions causes the syngas supply to go low, the heat from the stored steam or salt is used to heat the idle methanol reactors.

The synthesis reactor can catalytically reform the syngas or methanol using known processes to produce chemicals or liquid hydrocarbon fuels. The syngas can also be used to drive a gas turbine. The liquid hydrocarbon produced from the on-site fuel synthesis reactor is one or more of jet fuel, dimethyl ether (DME), gasoline, diesel, mixed alcohol, methanol, synthetic natural gas in liquid form, hydrocarbon chemicals, and heating oil. The on-site fuel synthesis reactor being integrated with the solar driven chemical reactor allows a fraction of the concentrated solar energy from the array of heliostats to be stored as an easily transportable and stable chemical energy source in the liquid hydrocarbon fuel form.

In an example, the solar generated syngas can be used with proven catalytic processes into intermediate methanol, and then subsequently into gasoline via the MTG process. Thus, The final product from this plant will be gasoline, produced by the commercial zeolite MTG process from the intermediate methanol product. Transportation quality gasoline can be produced from the methanol generated by the solar thermal process.

In an embodiment, the chemical plant is an integrated biorefinery that converts biomass-to-gasoline based on a solar thermal chemical reactor platform. The integrated biorefinery performs solar thermochemical biomass gasification to synthesis gas with a subsequent catalytic conversion of the synthesis gas to methanol, followed by the Methanol To Gas process to produce gasoline. The process uses concentrated solar thermal power to provide the energy needed to drive the gasification process as well as other integrated process through the use of waste heat.

Figure 8:
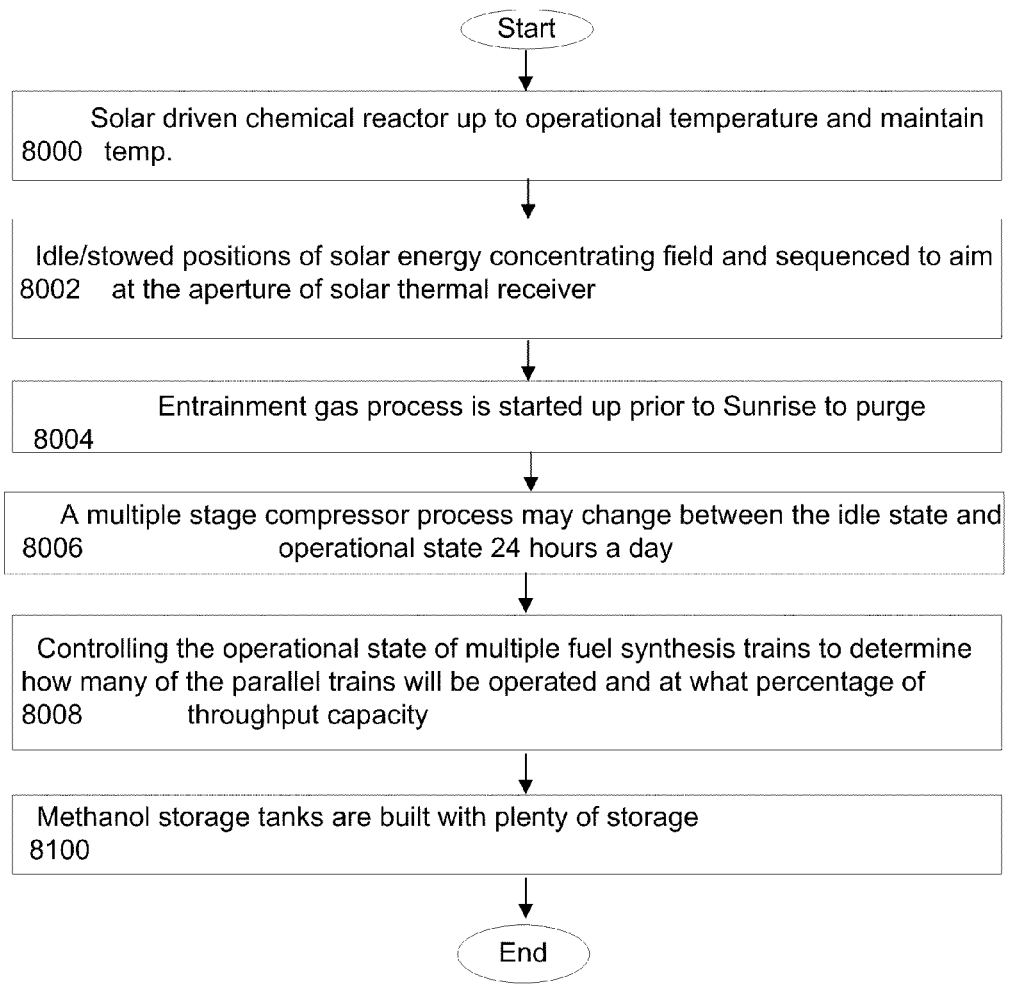
FIG. 8 illustrates a startup sequence of the integrated chemical plant.

FIG. 8 illustrates a startup sequence of the integrated chemical plant.

The Third Design Mechanism of the Start-Up Sequence

The startup sequence and order for the process steps and components making up the integrated solar driven chemical plant may be as follows. Many process steps may be started up or run in parallel. Some example sequences are as follows.

The main focus is getting the solar driven chemical reactor process 8000 up to operational temperature to drive various chemical reactants put into the chemical reactor in order to come out as desired reaction products with certain concentrations and quality. Thus, heat from the solar concentrating field and/or supplemental heat sources is used during start up of the integrated chemical plant to raise the chemical reactor to get up to an operational temperature of at least 800 degrees C. so that the effluent reactant products from the chemical reactor possesses a proper gas composition and quality for methanol synthesis.

After the time that the chemical reactor is up to the operational temperature, a control system then controls one of 1) a variable amount of reactor tubes participating in the reaction process, 2) a feed rate of biomass particles supplied into the reactor tubes of the chemical reactor from a feed system, or 3) both, in order to control flow rates of mass and chemical composition into the solar driven chemical reactor to 1) an available amount and 2) a predicted amount of concentrated solar energy available to drive the chemical reactions occurring in the chemical reactor while maintaining temperature of the chemical reactor between 800-1600 degree Celsius.

Insulation, an automated door, and supplemental heating for the solar thermal receiver are used to try to the solar driven chemical reactor located within a solar thermal receiver at a higher temperature above ambient during the periods of time when the chemical reactor stops commercial level production of syngas reaction products, such as at Sunset, and prior to when the chemical reactor resumes commercial level production of syngas reaction products, such as at or near Sunrise. Near Sunrise generally may be within 90 minutes of sunrise depending upon the weather and time of year. The covering, such as the automated door, closes over the apertures or other areas of heat loss after the commercial level production of reaction products stops, such as at or near Sunset or during extended weather events, and open/uncovers in the preparation stage to aiming the solar energy concentrating field at the aperture of the solar thermal receiver. Supplemental heat methods, such as electrical or steam heaters, may be used to elevate temperature of the solar driven reactor above atmospheric temperature and near an operating temperature of the reactor, at or near Sunrise as well during an extended weather event.

The solar energy concentrating field, such as heliostats, 8002 are taken out of the idle/stowed positions and sequenced to aim at the aperture of solar thermal receiver. Unstowing, calibrating the concentrating field, aiming each heliostat at the receiver, and verifying the integrity/operational state of the heliostats occur prior to or around Sunrise.

The entrainment gas process 8004 is started up prior to Sunrise to purge existing gases from the feed lines, reactor tubes, and possibly the syngas clean up tubes. Note, in an embodiment, the entrainment gas may be natural gas and/or steam, which is recirculated during start up from the effluent stream leaving the chemical reactor and the stored syngas is used to flow through and purge the syngas clean up tubes. The syngas may be recirculated back to the input of the reactor along with the entrainment gas.

The entrained-flow of biomass particles into the chemical reactor starts when 1) the solar energy concentrating field is aligned at the aperture of the solar thermal receiver containing the solar driven chemical reactor, and 2) the solar driven chemical reactor is at least a minimum operational temperature of 800 degrees Celsius and preferably greater than 1000 degrees Celsius.

The entrainment gas may purge the feed system, chemical reactor, and gas clean up system. It does not take long to gain enough velocity to entrain the biomass particles.

The process may flare and burn gases coming out of the system at start up until the syngas or other chemical product has the right composition. A composition analyzer feeds back parameters, such as $CO_2$ and tar, have the right composition and concentration. Alternatively, a recirculation line may run the effluent gases at start up back into the solar driven reactors input. Flaring of gases allows the start up gases to be run off to be burned off to atmosphere.

After the chemical reactor gets up to operational temperature, the control system controls an amount of tubes participating in the reaction process or biomass particles feed rate in the feed system to control flow rates of mass in and chemical composition of chemical reactants and possible inert particles into the solar driven chemical reactor to an available amount and predicted amount of concentrated solar energy available to drive the reactions and maintain temperature in an operational range. The number of reactor tubes supplying chemical reactants into the solar driven chemical reactor may be controlled individually, or preferably in groups/clusters of reactors.

The grinding system like the other process components supplying chemical reactants for chemical reactions to be conducted in the solar driven chemical reactor operates as a need be basis and up to 24 hours a day. The onsite storage of chemical reactants may be designed for a few days of operation at 100 percent capability for all of the multiple solar driven chemical reactors on-site.

The quenching, gas clean up, and ash removal process of the effluent gases coming out of the solar driven chemical reactor can be operated in an idle or operational state 24 hours a day. The system may run syngas from storage through the clean up system if an amine unit or other filter component needs to have its temperature and pressure maintained to preserve its filter medium or the system needs to prevent corrosion of the walls of its piping and tanks.

Figure 10:
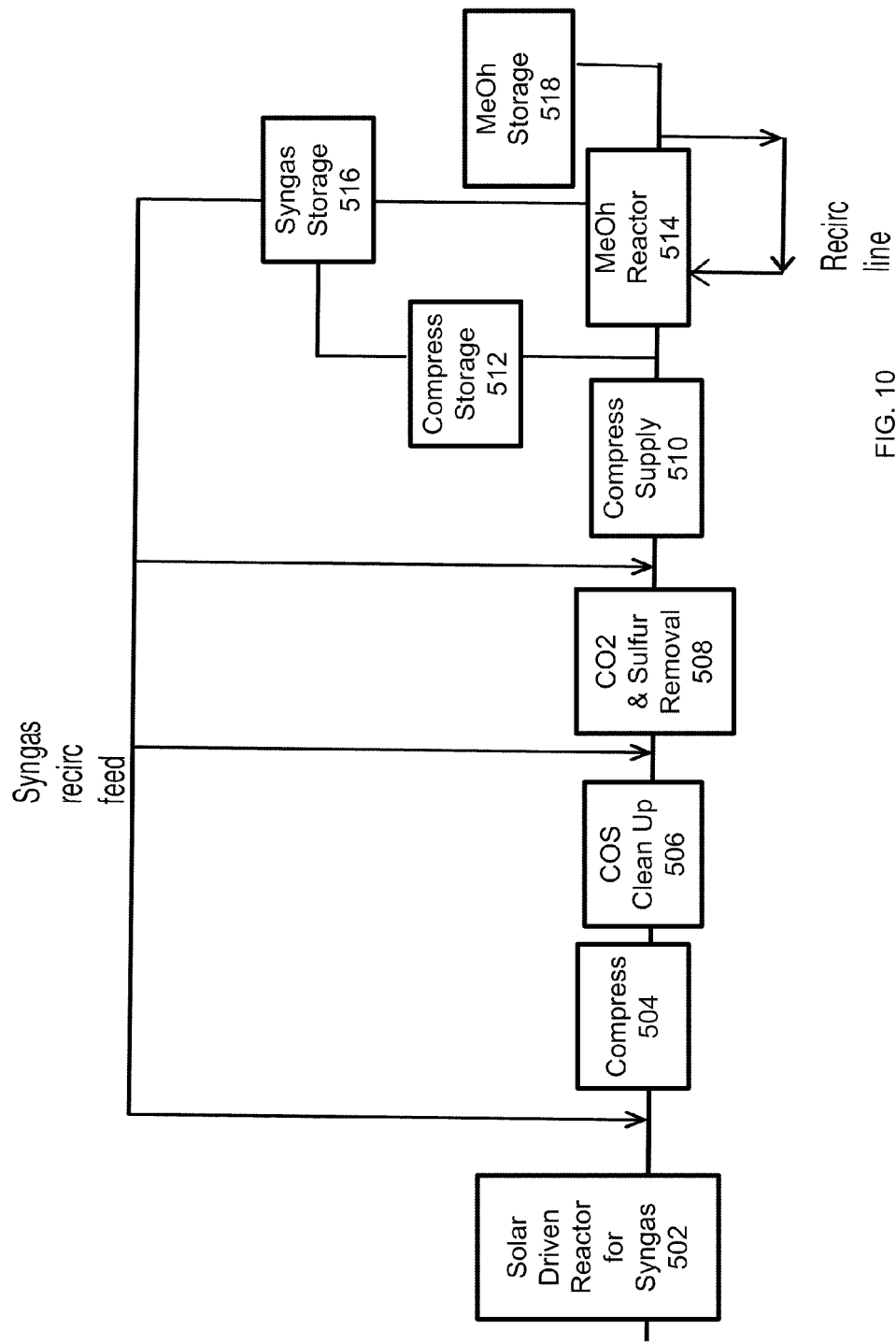
FIG. 10 illustrates a flow diagram of an embodiment of the syngas and methanol buffering and recirculation processes.

A multiple stage compressor process 8006 may change between the idle state and operational state 24 hours a day. The compressor set pressurizes syngas in different stages in the plant. See FIG. 10. The first compressor located after the quench unit starts compressing to feed the syngas stream to the $CO_2$ and sulfur remediation units, such as an amine plant. The second compressor directly feeds syngas to a methanol synthesis unit and brings the pressure to that required for methanol synthesis. The control system has a third compressor to send the remainder of the syngas to a storage unit. The control system determines the distribution to the compressor sets based on storage planning and synthesis needs. Generally, the compressor will recirculate syngas from the storage tank as a way to maintain an idle state but be ready to operate 24 hours a day.

Also, a syngas storage unit before the $CO_2$ and sulfur plant allows for the $CO_2$ and units to be significantly smaller in size/capacity may as well exist to account for diurnal events placed before a CO2 and sulfur removal plant. The syngas from the syngas storage unit may be recirculated through these CO2 and sulfur remediation units to place the sulfur and CO2 levels in the syngas into acceptable limits. As discussed, alternatively the start up gases may also be flared and burned in the atmosphere to place the, CO:H2 ratio, tar levels, sulfur and CO2 levels in the syngas into acceptable limits. In an embodiment, the syngas storage unit is sized to operate the methanol synthesis plant for 1 hour at 100 percent peak output without receiving supplemental syngas coming out of the solar driven chemical reactor.

Note, by operating all the time, the electrical start up load power draw is much less from some process steps. Further, by maintaining near operational temperature and pressure can prevent degradation of the catalyst and corrosion of plant components.

The control system 8008 controls the operational state of multiple fuel synthesis trains to determine how many of the parallel trains will be operated and at what percentage of throughput capacity of the methanol synthesis plant for a variable amount of syngas fed into the process. The methanol synthesis plant may control chemistry, temperature, and pressure parameters during cyclic operation of the methanol synthesis plant with little to no loss in catalytic activity or throughput over the plant's lifetime. The methanol synthesis plant uses 1) recycling of effluent stream from the methanol trains, 2) solar generated syngas directly from the gas clean up portion, and 3) supplemental syngas from syngas storage to operate in some capacity 24 hours a day. Note, at start up of the methanol plant, the methanol the effluent product gases can be flared and burned or recycled until the product gas achieves the right composition.

The methanol storage tanks 8100 are built with plenty of storage for methanol as an end product or intermediate chemical compound to another hydrocarbon fuel such as gasoline. The methanol synthesis plant has a much larger capacity, when operated at 100 percent capacity, than the methanol-to-gas synthesis plant. The excess methanol due to the larger capacity is built into the tanks is stored for overnight use while the remainder of the methanol goes to supply the methanol-to-gas synthesis plant during normal hours of operation from close to Sunrise to close to Sunset. When during off hours, the methanol-to-gas synthesis plant has a capacity to continue to run at a reduced percentage of peak capability from the methanol buffered and stored in the built methanol storage tanks. Thus, the MTG plant is designed and built to run at some dynamic range 24 hours a day, with the methanol liquid storage having enough capacity to run the MTG plant.

Additional Comments on the Design Mechanism of Decoupling the Process Steps

Thus, the two major sections exist in the integrated solar driven chemical plant, such as a biorefinery, are 1) feedstock preparation and supply, chemical reactions, and then syngas cleanup (the "front-end") and 2) chemical product production such as fuel synthesis and storage of the chemical product (the "back-end"), which are integrated by the supply of the solar generated products from the chemical reaction in the chemical reactor, such as syngas, but have some operational decoupling components built in. As discussed already, many decoupling mechanisms have been built into this integrated plant.

Some examples include the following.

Creating an excess generation of syngas from the chemical reactor at 100 percent capacity compared to the processing capability of the downstream fuel synthesis plant, such as the methanol plant. Building in storage capacity for the excess synthesis gas helps separate production generation from supply needs. Supplying syngas from storage and idling of the methanol trains to decouple a response rate of the methanol synthesis plant from the response rate of the solar driven chemical reactor. The storage capacity and idling processes established for the integrated solar driven chemical plant also decouples the direct production rate of the synthesis gas generated in the solar driven chemical reactor from the supply requirements of the methanol synthesis plant. The methanol synthesis plant makes liberal use of the stored syngas and recirculation lines to keep one or more methanol reactor train operational at some percent of maximum throughput while idling other trains based on current and predicted available syngas.

The stages of compressors are decoupled from a need for direct syngas generation by putting a recirculation line in from syngas storage to keep syngas flowing through the compressors when they idle.

The operation of the concentrating solar field can be decoupled from maintaining reactor operation in a limited function because the integrated plant has supplemental heating of the chemical reactor to keep the reactor near operational temperature at start up and the automatically controlled door on the receiver controls heat loss from the receiver and reactor during periods of shutdown.

Figure 9:
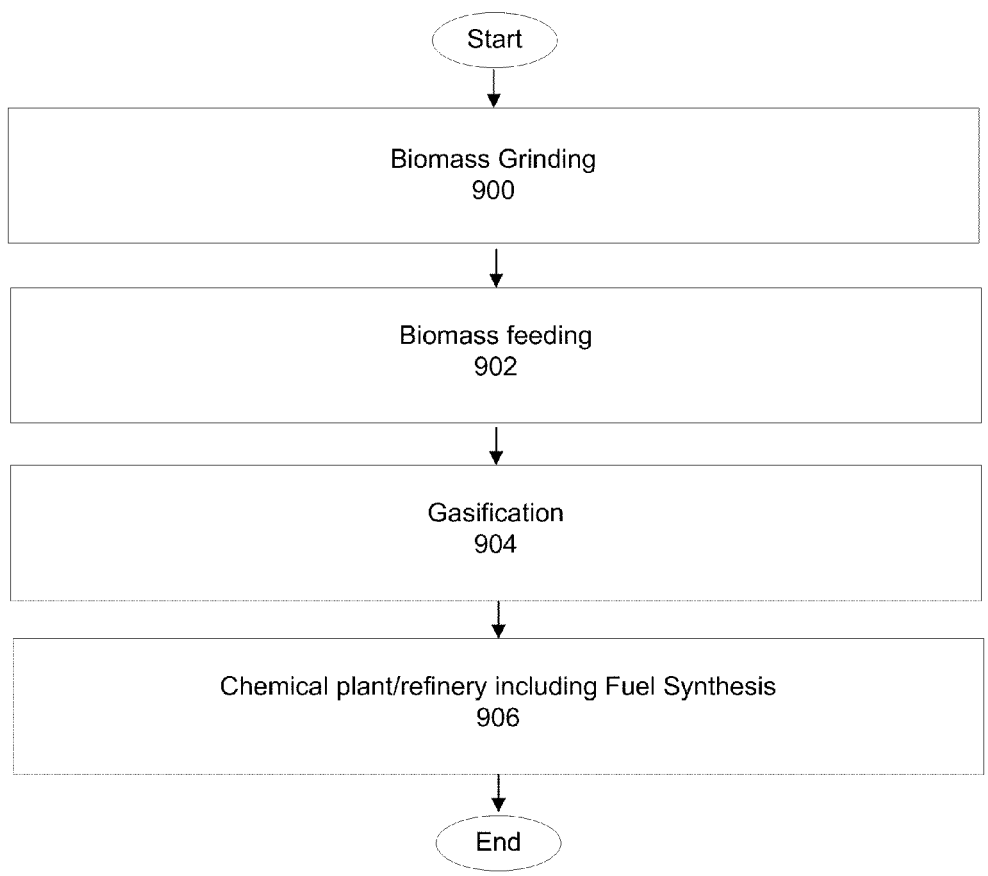
FIG. 9 illustrates a flow diagram of an embodiment of the system

FIG. 9 illustrates a flow diagram. In step 900, biomass grinding can occur. Equipment generally used for grinding biomass includes impact mills (e.g. hammer mills), attrition mills, and kinetic disintegration mills (e.g. flail mills). A hammer mill system can be used to grind the bales (loaded by conveyer) into primary particles. The re-ground particles have an average size between 500 um and 1000 um, and are loaded into the lock hopper system with a standard belt conveyer.

In step 902 biomass feeding occurs. In some embodiments, high pressure feeding may be used. High pressure feeding of solids of biomass with gasification at pressure may reduce capital cost due to the ability to use smaller compressors in some such systems. The lock hopper system can feed the reactor processes at pressure. For example, the feeding system can entrain the biomass materials in steam at high pressure, successfully disengage the particulates in the cyclone system, and distribute flow appropriately to the reactor tubes.

In step 904, gasification occurs. For example, in some embodiments, concentrated solar thermal energy drives gasification of the particles of the biomass to generate at least hydrogen and carbon monoxide products from the gasification reaction.

In step 906 fuel synthesis occurs. An on-site fuel synthesis reactor can receive the hydrogen and carbon monoxide products from the gasification reaction and use the hydrogen and carbon monoxide products in a hydrocarbon fuel synthesis process to create a liquid hydrocarbon fuel.

Some embodiments of the solar-driven chemical plant include a spray nozzle to supply water to the product gas exiting the chemical reactor to shift some of the product carbon monoxide to additional hydrogen and carbon dioxide gas in a water gas shift reaction, making the hydrogen to carbon monoxide ratio appropriate for methanol synthesis, such as a H2:CO ratio in the synthesis gas within the range 2.0 to 2.7.

The methods and apparatuses of the invention in some cases may be implemented using computer software. If written in a programming language conforming to a recognized standard, sequences of instructions designed to implement the methods can be compiled for execution on a variety of hardware platforms and for interface to a variety of operating systems. It will be appreciated that a variety of programming languages may be used to implement the teachings of the invention as described herein. Furthermore, it is common in the art to speak of software, in one form or another (e.g., program, procedure, application, driver, etc.), as taking an action or causing a result. Such expressions are merely a shorthand way of saying that execution of the software by a computer causes the processor of the computer to perform an action or produce a result.

The control system may operate in a networked environment using logical connections to one or more remote computers, such as a remote computer. The remote computer may be a personal computer, a hand-held device, a server, a router, a network PC, a peer device or other common network node, and typically includes many or all of the elements described above relative to the computer.

A machine-readable medium is understood to include any mechanism for storing or transmitting information in a form readable by a machine (e.g., a computer). For example, a machine-readable medium includes read only memory (ROM); random access memory (RAM); magnetic disk storage media; optical storage media; flash memory devices, etc.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. These routines, algorithms, etc. may be written in a number of different programming languages. Also, an algorithm may be implemented with lines of code in software, configured logic gates in software, or a combination of both. The portable application and its security mechanisms may be scripted in any number of software program languages. Unless specifically stated otherwise as apparent from the above discussions, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers, or other such information storage, transmission or display devices.

While some specific embodiments of the invention have been shown the invention is not to be limited to these embodiments. The invention is to be understood as not limited by the specific embodiments described herein, but only by scope of the appended claims.

We claim:

1. A method for an integrated chemical plant, comprising:
converting a chemical reactant, including particles of biomass, in a radiant heat driven chemical reactor into synthesis gas containing carbon monoxide and hydrogen using radiant heat energy to drive the conversion of the chemical reactant;
supplying the synthesis gas for a catalytic conversion of the synthesis gas in a methanol synthesis plant to methanol;
gasifying the particles of biomass in multiple reactor tubes of the chemical reactor in the presence of one or more of the following chemical reactants in the tubes: (i) biomass particles and steam (ii) biomass particles, methane, and steam, (iii) methane and steam (SMR), wherein the inside walls of the reactor tubes are made of corrosion resistant materials with a resistance to steam of between a good to excellent rating;
injecting a cooling compound into an effluent stream including reaction products exiting the multiple reactor tubes to simultaneously 1) rapidly cool at least H2 and CO in the reaction products from the at least 1000 degree C. to less than 400 degrees C. and 2) provide chemical compounds necessary to achieve a proper H2 to CO ratio of syngas necessary for fuel synthesis; and
where a control system for the chemical reactor sends control signals to and receives feedback from a control system for the methanol synthesis plant.

2. The method for the integrated chemical plant of claim 1, further comprising:
cycling between an operational state and an idle state for a number of methanol trains in the methanol synthesis plant depending upon an amount of synthesis gas generated in the solar driven chemical reactor, and wherein the radiant heat driven chemical reactor is a solar-driven chemical reactor aligned to receive concentrated solar thermal energy from one or more solar energy concentrating fields including an array of heliostats, solar concentrating dishes or any combination of these two.

3. The method for the integrated chemical plant of claim 2, further comprising:
creating a storage capacity of the synthesis gas and idling of the methanol trains to decouple a response rate of the methanol synthesis plant from the response rate of the solar driven chemical reactor, and wherein the storage capacity and idling processes established for the integrated chemical plant also decouples a direct production rate of the synthesis gas generated in the chemical reactor from the supply requirements of the methanol synthesis plant.

4. The method for the integrated chemical plant of claim 2, further comprising:
balancing chemical reaction types, including a biomass gasification reaction, a stream reforming reaction, a dry reforming reaction and various combinations of these reactions within the solar driven chemical reactor, to an amount of concentrated solar energy available directed at a solar thermal receiver containing the chemical reactor in order to keep the solar chemical reactor at a temperature at which the chemical reactor operates high enough to maintain the generated syngas within the desired molar ratio of H2 to CO ratio of 2.1:1 to 2.8:1 with being substantially tar free having less than 200 mg/m^3 of tar, and having less than 15% by volume CO2 in the generated syngas; and
controlling an amount of steam, natural gas, and biomass particles, flowing in the reactor tubes of the chemical reactor to keep the generated syngas within the above set thresholds.

5. The method for the integrated chemical plant of claim 2, further comprising:
during start up of the integrated chemical plant raising the chemical reactor to get up to an operational temperature of at least 800 degrees C. so that the effluent reactant products from the chemical reactor possesses a proper gas composition and quality for methanol synthesis; and after the time that the chemical reactor is up to the operational temperature, controlling one of 1) a variable amount of reactor tubes participating in the reaction process, 2) a feed rate of biomass particles supplied into the reactor tubes of the chemical reactor from a feed system, or 3) both, in order to control flow rates of mass and chemical composition into the solar driven chemical reactor to 1) an available amount and 2) a predicted amount of concentrated solar energy available to drive the chemical reactions occurring in the chemical reactor while maintaining temperature of the chemical reactor between 800-1600 degree Celsius.

6. The method for the integrated chemical plant of claim 2, further comprising:
keeping the solar driven chemical reactor located within a solar thermal receiver at a higher temperature above ambient during the periods of time when the chemical reactor stops commercial level production of syngas reaction products and prior to when the chemical reactor resumes commercial level production of syngas reaction products.

7. The method for the integrated chemical plant of claim 2, wherein different reactor tubes within the same receiver are constructed of a material to operate with the different chemical reactants, and wherein the chemical plant is an integrated biorefinery that converts the particles of biomass-to-gasoline in the integrated chemical plant, where the methanol from the methanol synthesis plant is converted to gasoline in a methanol-to-gas process.

8. The method for the integrated chemical plant of claim 2, wherein a thick layer of insulation around a solar thermal receiver containing the chemical reactor is set to limit heat losses by conduction from a cavity of the receiver in conjunction with a moveable insulative door that covers a receiver aperture to limit heat losses by radiation, conduction, and convection from leaving the cavity during periods of non-operation, including inclement weather or nighttime, so that the temperature in the cavity is decreased by less than 400° C. in a 12 hour period when no concentrated solar energy is directed at the cavity aperture, where the insulation and door maintain heat energy to reduce both 1) the amount of time required to heat the receiver and reactor tubes following a down period and 2) the thermal shock and stresses imparted to the receiver and reactor materials of construction.

9. The method for the integrated chemical plant of claim 1, further comprising:
locating a quench zone near an exit of a gasification reaction zone of the reactor tubes in the chemical reactor, where one or more injection pipes in the quench zone directly inject the cooling compound consisting of at least one of 1) low temperature water ($H_2O$), 2) methane ($CH_4$) with low temperature water, 3) low temperature methanol ($CH_3OH$), and 4) various combinations into the syngas tubes and/or manifold carrying the effluent stream of the reactor tubes to simultaneously 1) rapidly cool the syngas stream of reaction products from the at least 1000 degree C. to less than 400 degrees C. and 2) provide chemical compounds necessary to achieve a proper H2 to CO ratio of syngas necessary for fuel synthesis, and where the energy to cause the endothermic reactions comes from heat contained in the reaction product syngas stream, and the proper H2 to CO ratio of syngas composition necessary for fuel synthesis is a 2:1 to 2.8:1 H2 to CO ratio.

10. The method for the integrated chemical plant of claim 2, further comprising:
operating multiple methanol reactor trains in parallel from an input supplied with syngas from either 1) the solar driven chemical reactor 2) from a syngas storage unit, or a combination of both; and
controlling the operation of the multiple trains by potentially 1) idling one or more of the methanol reactor trains or 2) reducing the output of one or more of the methanol reactor trains based on feedback from the amount of synthesis gas being generated by the solar driven chemical reactor, which is subject to marked variations in volume of syngas output based on a seasonal, diurnal and weather effects, and thus, the multiple methanol reactor trains are individually controllable to be cycled between the idle state and the operational state due to the variable amount of syngas being fed into the process from the solar driven chemical reactor.

11. The method for the integrated chemical plant of claim 10, further comprising:
controlling parameters including chemistry, temperature, and pressure of the methanol synthesis plant during idle non-production periods of time so that the methanol synthesis plant may rapidly resume to generating product methanol when the supply of solar generated syngas resumes in sufficient quantities;
controlling parameters including chemistry, temperature, and pressure of the methanol synthesis plant during idle non-production periods of time so that the methanol synthesis plant has little to no additional loss in catalytic activity or throughput over the plant's lifetime above expected losses from the catalyst aging and participating in the catalytic activity; and
supplying the synthesis gas from the solar driven chemical reactor to a downstream chemical synthesis processes, in which methanol is generated and then supplied to a Methanol-to-Gasoline process.

12. A method for an integrated chemical plant, comprising:
grinding biomass into particles that have an average smallest dimension size between 200 microns (um) and 2000 um in diameter, such to fit through the holes in the filters, with a general range of between 500 um and 1000 um;
supplying, via two or more feed lines, particles of biomass having the average smallest dimension size between 50 microns (um) and 2000 um to a radiant heat driven chemical reactor;
using an entrained carrier gas to move the biomass particles into the radiant heat driven chemical reactor;
conducting a chemical reaction in the radiant heat driven chemical reactor having multiple reactor tubes using the radiant heat energy to drive the conversion of the chemical reactant, wherein an endothermic chemical reaction conducted in the reactor tubes includes one or more of the following: biomass gasification, steam methane reforming, and methane cracking; and
injecting a cooling compound into an effluent stream including reaction products exiting the multiple reactor tubes to simultaneously 1) rapidly cool at least H2 and CO in the reaction products from at least 1000 degree C. to less than 400 degrees C. and 2) provide chemical compounds necessary to achieve a proper H2 to CO ratio of syngas necessary for fuel synthesis.

13. The method for the integrated chemical plant of claim 12, further comprising:
using solar energy coming from a concentrated solar energy field to drive the reactions in the chemical reactor, where the endothermic chemical reaction conducted in reactor tubes is a biomass gasification reaction, a stream reforming reaction, a dry reforming reaction and various combinations of these reactions within the solar driven chemical reactor, where control of the multiple reactor tubes is split into two or more groups of tube subsets;

a control system for the chemical synthesis plant sending control signals to and receiving feedback from a control system for the chemical reactor, and the control system for the chemical reactor at least indicating the amount of product being generated in the solar driven chemical reactor; and balancing an amount of the biomass particles flowing into each of the reactor tubes to an amount of solar energy available by controlling a rotational rate of a screw of a lock hopper feeding the biomass particles to an entrainment gas that carries the biomass particles to the reactor tubes, where all of the reactor tubes in tube subset being supplied by this lock hopper have their feed rate simultaneously turned up or turned down;

supplying the products from the chemical reaction to a downstream chemical synthesis plant that has its operating and idle parameters controlled to account for the cyclic supply of solar generated products from the solar driven chemical reactor as a feed product; and starting an entrained-flow of chemical reactants into the chemical reactor when 1) the solar energy concentrating field is aligned at an aperture of the solar thermal receiver containing the solar driven chemical reactor, and 2) the solar driven chemical reactor is at at least a minimum operational temperature of 800 degrees Celsius and preferably greater than 1000 degrees Celsius.

14. The method for the integrated chemical plant of claim 12, further comprising:

using solar energy coming from a concentrated solar energy field to drive the reactions in the chemical reactor, where the endothermic chemical reaction conducted in reactor tubes is a biomass gasification reaction, a stream reforming reaction, a dry reforming reaction and various combinations of these reactions within the solar driven chemical reactor; and balancing of mass in and energy needed to drive various chemical reactions verses available concentrated solar energy while still maintaining operational temperature of the chemical reactor within a set range and factoring in that each endothermic reaction consumes an amount of available energy AND controlling a concentration/amount of each reactant product into the chemical reactor to control the molarity and ratio of the reactants going into the reactions in order to control the products coming out of the reactions, AND controlling what chemical reactants are being supplied to the reactor; and thus, what chemical reactions are occurring within multiple reactor tubes.

15. The method for the integrated chemical plant of claim 12, further comprising:

where the endothermic chemical reaction conducted in reactor tubes is a biomass gasification reaction, a stream reforming reaction, a dry reforming reaction and various combinations of these reactions within the chemical reactor; and using a combination of controlling an amount of steam, natural gas, biomass particles, other chemical reactants, and inert particles flowing in the tubes to keep the generated syngas within set thresholds.

16. The method for the integrated chemical plant of claim 12, further comprising:

using solar energy coming from a concentrated solar energy field to drive the reactions in the chemical reactor, where the endothermic chemical reaction conducted in reactor tubes is a biomass gasification reaction, a stream reforming reaction, a dry reforming reaction and various combinations of these reactions within the solar driven chemical reactor;

controlling a feed rate of particles of biomass in the solar driven chemical reactor by a feedforward/feedback model-predictive control system in cooperation with designing in enough surface area, thermal mass, and heat capacity in the multiple tubes and receiver cavity to ensure that temperature of the reactor cavity remains in the operational temperature range of below 1600 degrees C. and above 800 degrees C. during the rapidly changing daily weather conditions, where a feed forward model predicts an available solar energy over each time period in a given day based on anticipated weather, where enough surface area and thermal mass are designed/built into a cavity of a solar receiver and the multiple reactor tubes of the chemical reactor, to act as a ballast, averaging out very short term small fluctuations (second to second) in the available solar energy to cause a negligible ramp-up and ramp-down of temperature of the receiver and reactor due to these instantaneous changes in available solar energy;

analyzing a chemical composition at the exit of the chemical reactor to sense changes for one or more possible effluent chemicals including hydrogen, carbon monoxide, methane, tar composition, carbon dioxide, sulfide or any combination thereof; and providing a dynamic signal to the feedback portion of the control system to keep these above compositions stay within the desired ranges.

17. The method for the integrated chemical plant of claim 12, further comprising:

using solar energy coming from a concentrated solar energy field to drive the reactions in the chemical reactor, where the endothermic chemical reaction conducted in reactor tubes is a biomass gasification reaction, a stream reforming reaction, a dry reforming reaction and various combinations of these reactions within the solar driven chemical reactor, and the fuel synthesis plant is a methanol synthesis plant;

supplying a control signal to and receiving feedback from 1) a chemical reactant feed system, 2) a solar energy concentrating field, 3) a supplemental heating system for idle periods, and 4) the methanol synthesis plant; and where the lag times and the response times of the 1) solar energy concentrating fields to alter alignment and an amount of concentrated solar energy supplied, 2) the feed system to alter an amount of biomass flowing in the reactor tubes, 3) time for weather events to alter an amount of solar energy available, and 4) time to alter syngas composition including H2:CO ratio for methanol synthesis are all factors taken into account by a control algorithm in the control system in sending out the control signals to the feed system, the solar energy concentrating fields, the methanol synthesis plant, and the supplemental heating system.

* * * * *